United States Patent [19]

Tsuji et al.

[11] Patent Number: 4,884,134
[45] Date of Patent: Nov. 28, 1989

[54] VIDEO ENDOSCOPE APPARATUS EMPLOYING DEVICE SHUTTER

[75] Inventors: Kiyoshi Tsuji, Tana; Kenji Kimura, Tachikawa; Yoshihiro Okada, Hachioji, all of Japan

[73] Assignee: Olympus Optical Co., Ltd., Tokyo, Japan

[21] Appl. No.: 238,061

[22] Filed: Aug. 30, 1988

[30] Foreign Application Priority Data

Oct. 7, 1987 [JP] Japan .................................. 62-254068
Apr. 19, 1988 [JP] Japan .................................. 63-97417

[51] Int. Cl.⁴ ............................ A61B 5/04; A61B 1/06
[52] U.S. Cl. .................................. 358/98; 358/213.24; 358/213.26; 358/213.27; 128/6
[58] Field of Search ................. 358/98, 213.24, 213.26, 358/213.27; 128/6

[56] References Cited

U.S. PATENT DOCUMENTS 4,631,593 12/1986 Kinoshita ..................... 358/213.24
4,704,633 11/1987 Matsumoto ................... 358/213.27
4,746,975 5/1988 Ogiu ............................. 358/213.26

FOREIGN PATENT DOCUMENTS 60-43711 9/1985 Japan .

Primary Examiner—Howard W. Britton
Attorney, Agent, or Firm—Armstrong, Nikaido Marmelstein Kubovcik & Murray

[57] ABSTRACT

An endoscope apparatus has a storage-time switching circuit for shortening the charge storage time of a solid state imaging device provided with a photoelectric conversion function, and the quantity of illuminating light to be projected an object is increased in association with the operation of this switching circuit. In this transient process of increasing the quantity of illuminating light, the level of video signals obtained by imaging is compared with a proper reference level. If the level of the video signals reaches the reference level, the video signals are stored in a storage circuit. Accordingly, it is possible to obtain a frozen picture which is scarcely blurred.

32 Claims, 18 Drawing Sheets

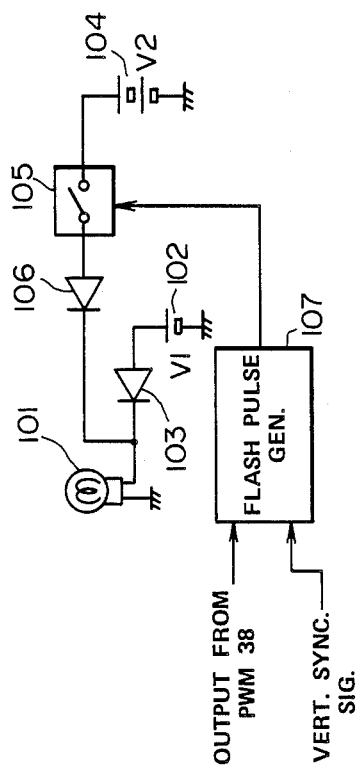
FIG. 8
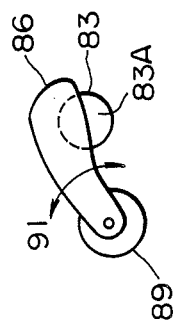
FIG. 7
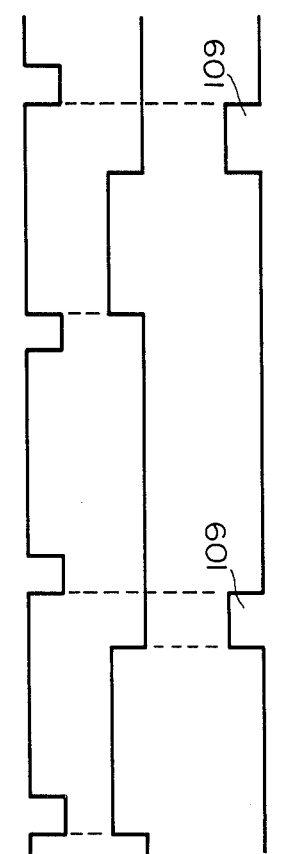
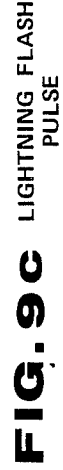
FIG. 9a  VERT. SYNC. SIG.
FIG. 9b  OUTPUT FROM PWM
FIG. 9c  LIGHTNING FLASH PULSE

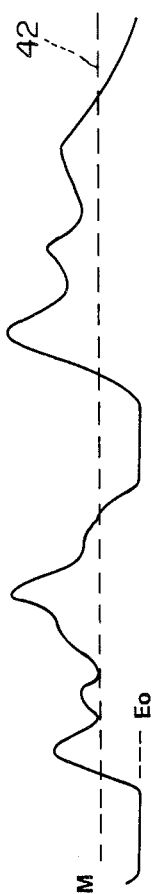
FIG.16 OUTPUT FROM CDS CC.
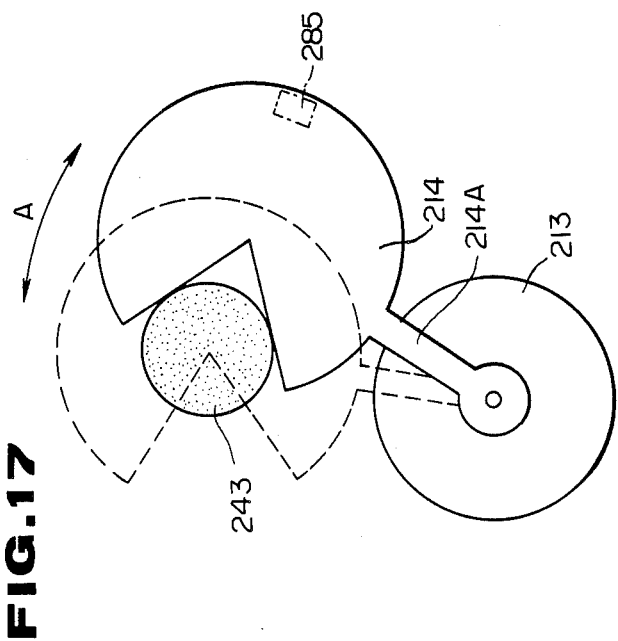
FIG.17

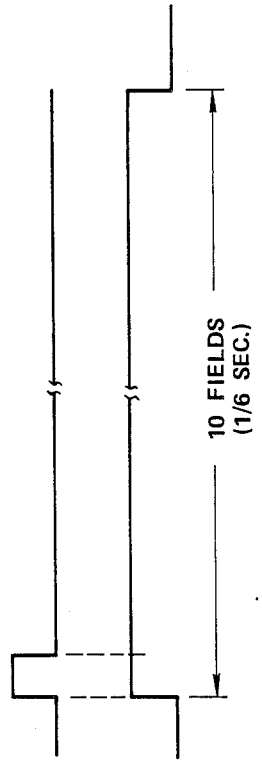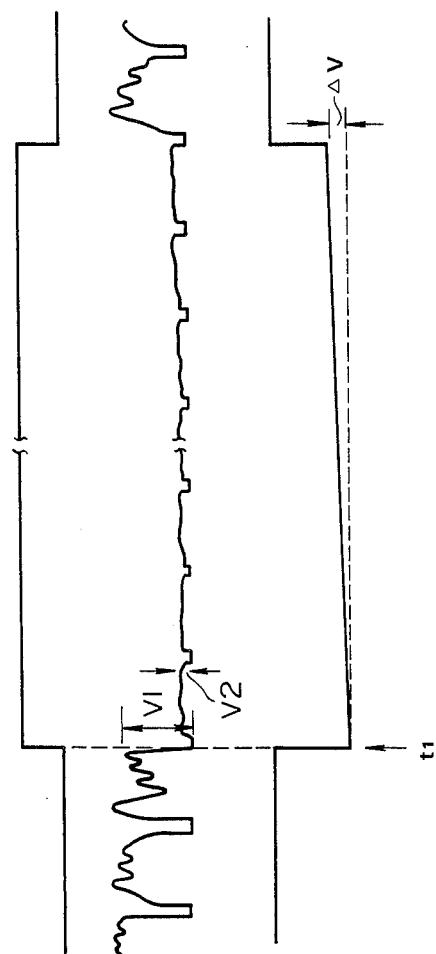

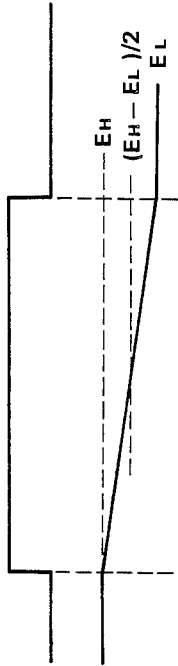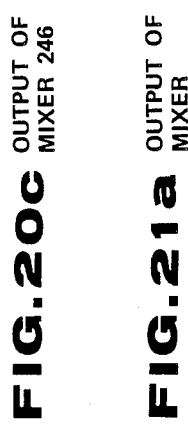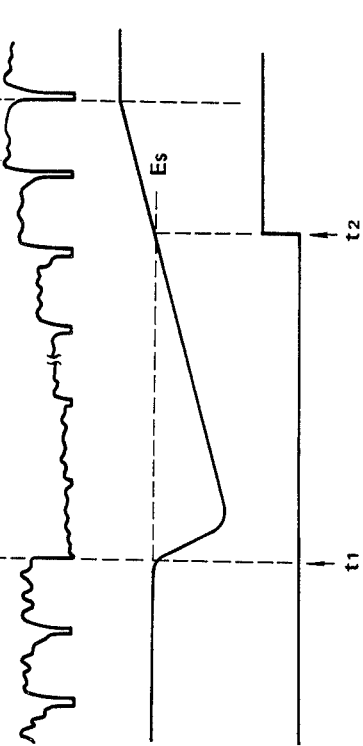
FIG.20a OUTPUT PULSE OF PULSE GEN. 252
FIG.20b OUTPUT OF 255
FIG.20c OUTPUT OF MIXER 246
FIG.21a OUTPUT OF MIXER
FIG.21b OUTPUT OF CDS CC.
FIG.21c OUTPUT OF DETECTOR
FIG.21d OUTPUT OF COMPARATOR

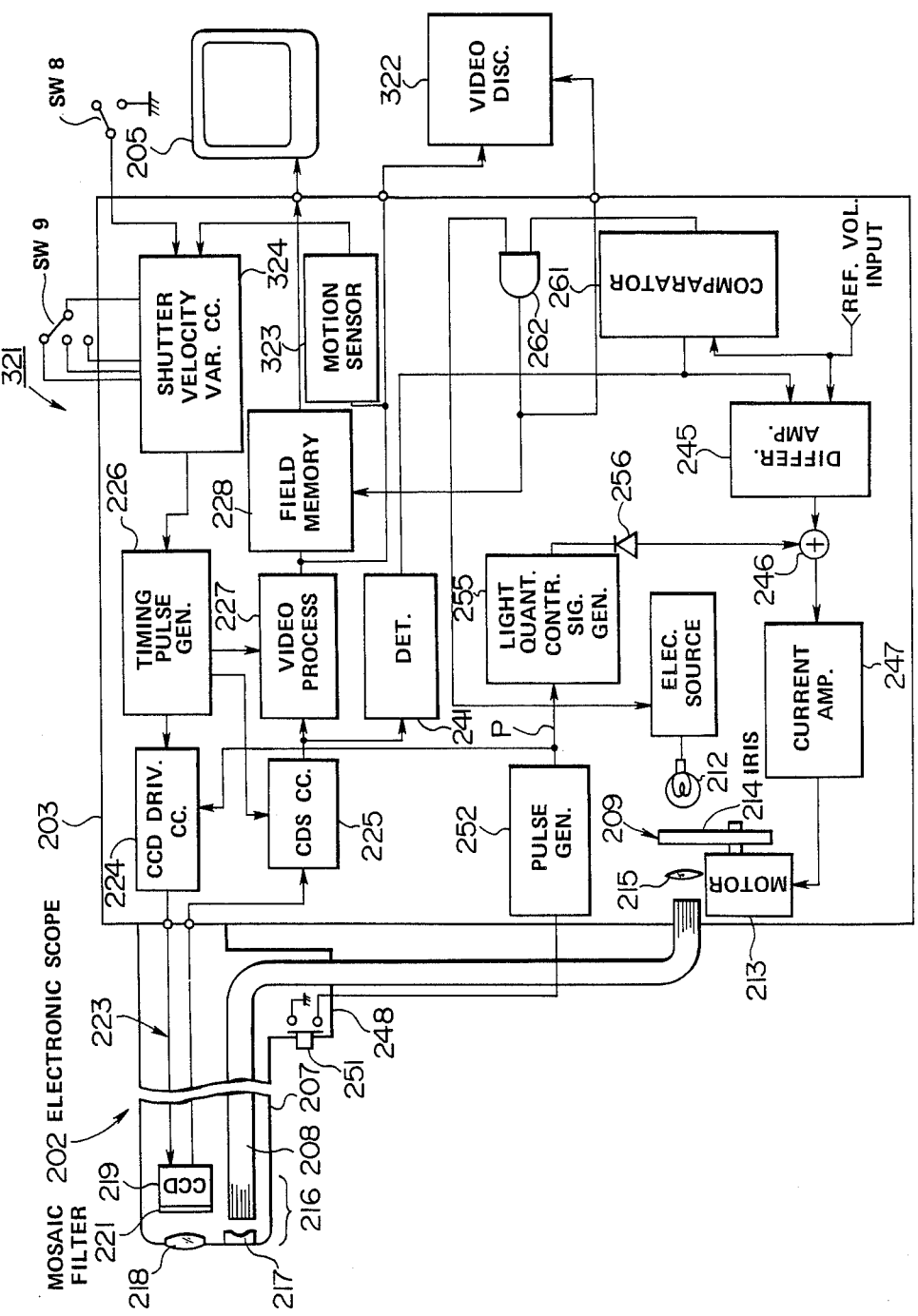

VIDEO ENDOSCOPE APPARATUS EMPLOYING DEVICE SHUTTER

BACKGROUND OF THE INVENTION

1. Field of the Invention

The present invention relates to a video endoscope apparatus employing a device shutter capable of preventing the occurrence of blurred images.

2. Description of the Related Art

In recent years, an electronic type of endoscope (such as an electronic scope) employing imaging means constituted by a solid state imaging device such as a charge coupled device (hereinafter referred to as the "CCD") has been used in practice.

Such an electronic scope has the advantage that recording and reproduction of images can be readily performed compared with those of an optical type of scope.

In a generally used method of driving a CCD, as is known, charges are stored (integrated) in each of photodiodes which constitute the CCD for approximately 1/60 seconds, and the thus-stored charges are read from the CCD at time intervals of 1/60 seconds to provide video signals. As a matter of course, if an object moves during the 1/60-second period required for charges to be stored, the obtained video signals become remarkably low in resolution, that is, the obtained image is blurred.

In the field of television cameras for home use, a so-called device shutter function is utilized to eliminate the above-described problem of blurred images. The device shutter is an electrical means for shortening the storage time so that a conventional storage time of 1/60 seconds (in a frame storage system, 1/30 seconds) is reduced to, for example, 1/600 seconds equivalent to one tenth of 1/60 seconds.

Japanese Patent Laid-open No. 121779/1980 discloses an endoscopic imaging apparatus arranged to store charges for one frame period or a plurality of frame periods in a television receiver whose frame period is fixed.

In this related art example, if an object to be imaged is moving, imaging (storage of charges) is performed for one frame period, while, if the quantity of light is insufficient, storage of charges is performed over a plurality of frame periods, whereby images which are high in S/N ratio can be obtained.

However, even this related art example cannot eliminate any blurred image which may occur within one frame period.

SUMMARY OF THE INVENTION

It is, therefore, an object of the present invention to provide a video endoscope apparatus capable of providing an endoscopic image which is scarcely blurred.

It is another object of the present invention to provide a video endoscope apparatus capable of providing a video endoscope apparatus capable of providing an endoscopic image which has appropriate contrast suitable for diagnosis even if a short shutter opening period is selected.

To achieve the above and other objects, in accordance with the present invention, there is provided a video endoscope apparatus including switching means for shortening a charge storage time, illuminating-light-quantity increasing means for forcibly increasing the quantity of light which illuminates an object, level detecting means for detecting whether or not the signal level provided by imaging when the quantity of illuminating light has been increased is a proper level, and storage means for storing video signals provided by a solid state imaging device when the level detecting means has determined that the signal level is the proper level. With this arrangement, it is possible to provide a frozen picture of the object which is high in S/N ratio and which is not blurred even if a short imaging period is selected.

The above and other objects and features of the invention will become apparent from the following detailed description of embodiments thereof taken in connection with the accompanying drawings.

BRIEF DESCRIPTION OF THE DRAWINGS

FIG. 7 is a front elevational view of a movable light shielding member for use in a light source device according to the second embodiment;

FIG. 8 is a circuit diagram showing the essential portion of a third embodiment of the present invention;

FIGS. 9a, 9b and 9c are timing charts which serve to illustrate the operation of the third embodiment;

FIG. 16 is a diagram showing the waveform of a video signal which is input to the video processing circuit according to the seventh embodiment;

FIG. 17 is a schematic view illustrating a light adjusting member according to the seventh embodiment;

FIGS. 18a and 18b are views illustrating how a pulse is output by operating a switch in the seventh embodiment;

FIGS. 19a, 19b and 19c are views which serve to illustrate the operation of an automatic light adjustment mechanism according to the seventh embodiment;

FIGS. 20a, 20b and 20c are views showing the output waveform of a light-quantity increasing signal which is output together with the pulse of a pulse generator according to the seventh embodiment;

FIGS. 21a to 21c are timing charts which serve to illustrate the operation when a special imaging mode is selected;

FIG. 29 is a block diagram showing a twelfth embodiment of the present invention.

DESCRIPTION OF THE PREFERRED EMBODIMENTS

Figure 1:
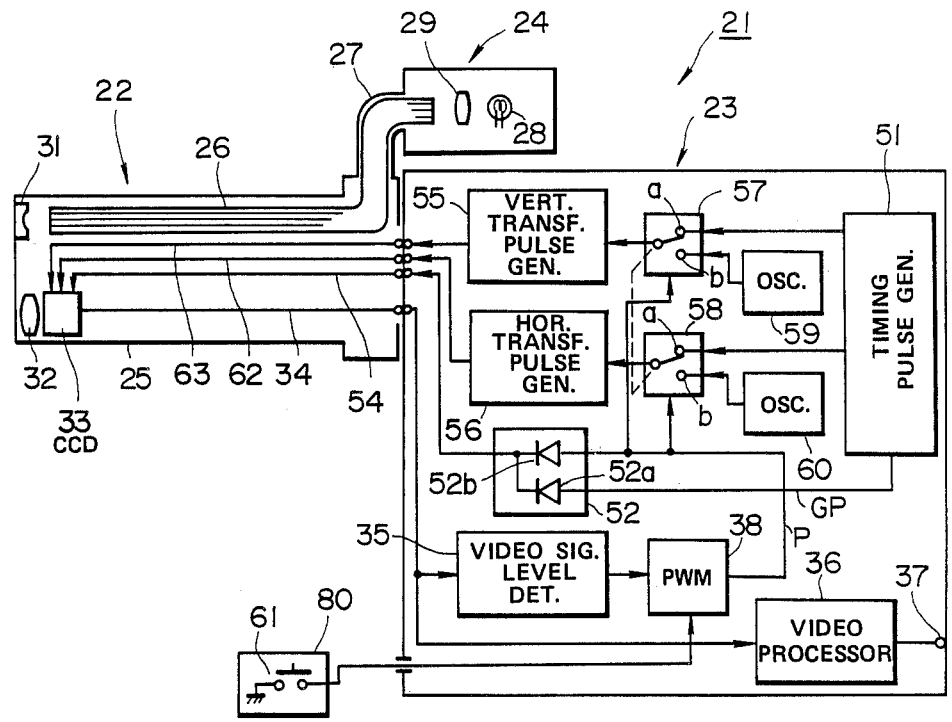
FIG. 1 is a block diagram of a first embodiment of the present invention.

Referring to FIG. 1, a video endoscope apparatus 21 according to a first embodiment of the present invention are generally composed of an electronic scope 22, a scope body 23 detachably connected to the electronic scope 22 and provided with a group of signal processing means, a light source device 24 for supplying illuminating light to the electronic scope 22, and a monitor (not shown) connected to the scope body 23 for providing a display of video signals.

The electronic scope 22 has an elongated inserting section 25 which can be inserted into a body organ, and a light guide 26 for transmission of illuminating light is inserted through the inserting section 25. The trailing end of the light guide 26 is inserted through a light guide cable 27 and attached to the light source device 24 so that the illuminating light can be supplied from the light source device 24. More specifically, white light emitted from a lamp 28 is focused on the surface of the entrance end of the light guide 26 by a condenser lens 29. The illuminating light incident upon this entrance end surface is transmitted through the light guide 26, passed through the surface of its leading end surface, and diverged by an projection lens 31 to illuminate an object. An image of the illuminated object is focused on a photosensitive surface of a solid state imaging device, for example, a CCD 33 by an objective lens 32 disposed at the leading end of the inserting section 25. The focused image is subjected to photoelectric conversion and stored in the CCD 33 in the form of charges. The photoelectrically converted signal output from the signal output terminal of the CCD 33 is transferred through a cable 34 to the body 23 and supplied to both a video-signal-level detector 35 and a video processor 36. The video processor 36 receives the output signal of the CCD 33, modulates it into a video signal according to a predetermined video format such as that of the NTSC system, and outputs the converted video signal to the monitor (not shown) through a video signal output terminal 37.

Figure 2:
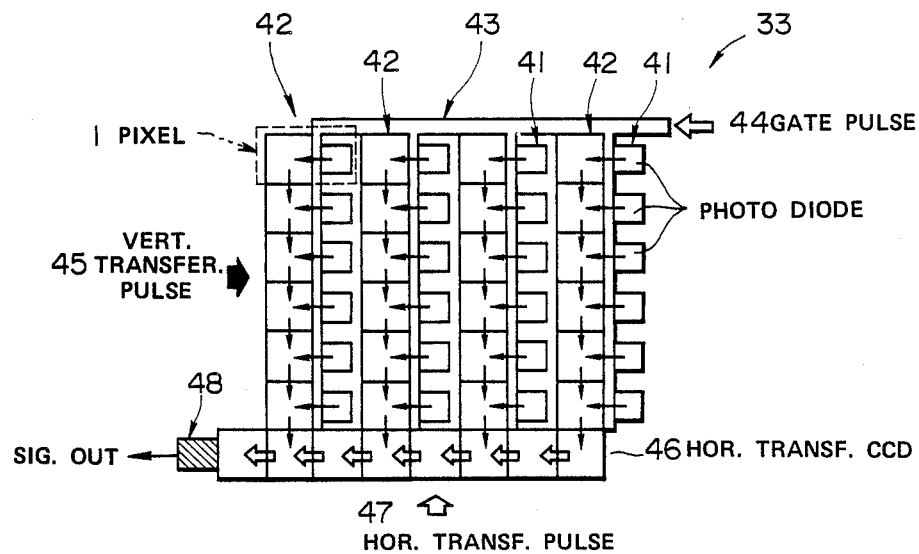
FIG. 2 is a schematic view illustrating the structure of a solid state imaging device for use in the first embodiment.

The video-signal-level detector 35 serves to detect the level of the output signal of the CCD 33 and convert the detected level into a DC signal. The detector 35 outputs a DC voltage proportional to the level of the output signal of the CCD 33, and this output is supplied to a PWM circuit (pulse width modulation circuit) 38 as a modulated input signal. The PWM circuit 38 is adapted to effect pulse width modulation so as to increase its output pulse width in proportion to the output level of the CCD 33. In this embodiment, its shutter function is realized by altering a method of driving the CCD 33 instead of providing the above-described conventional means for converting illuminating light supplied from the light source into intermittent illuminating light. More specifically, charges stored in photodiodes which constitute the CCD 33 are read out at high speed to inhibit the storage of charges for a predetermined time period, thereby controlling the storage time. The CCD 33 used in this embodiment is an interline transfer CCD having a construction such as that shown in FIG. 2. The interline transfer CCD 33 includes photosensitive portions (or photodiodes) 41 and vertical transfer CCDs (vertical transfer registers) 42, and the photosensitive portions 41 and the vertical transfer CCDs 42 are arranged in vertical columns, respectively, nd alternately in horizontal rows. A signal, which is photoelectrically converted and stored as charges in each of the photosensitive portions 41, is transferred to its adjacent vertical transfer CCD 42 by the application of a gate pulse 44 to a readout gate 43. Also, the signal transferred to the adjacent vertical transfer CCD 42 is transferred by one row in the vertical direction by the application of a vertical transfer pulse 45. The signals in the lowest row are transferred to a horizontal transfer CCD array (horizontal register array) 46. Also, when a horizontal transfer pulse 47 is applied to the horizontal transfer CCD array 46, each of the signals is transferred by one column in the horizontal direction. The signal in the leftmost column is output from an output portion 48.

Figure 3:
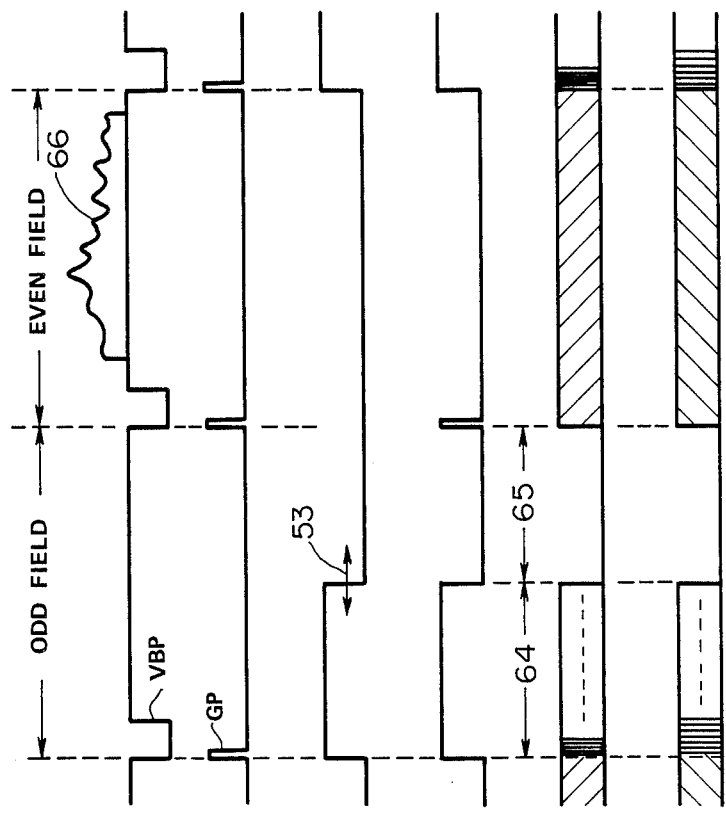
FIGS. 3a to 3f are timing charts showing the operation of the first embodiment.

In order to read signals from the above-described CCD 33, a timing pulse generator 51 is accommodated in the body 23. The timing pulse generator 51 outputs the GP pulse shown in FIG. 3b to a pulse mixer 52 during the leading edge of a vertical blanking period VBP of the video signal shown in FIG. 3a to apply the GP pulse to a diode 52a which forms a part of the pulse mixer 52. Also, a PWM circuit 52 applies a pulse P according to the output level of the CCD 33 to another diode 52b of the pulse mixer 52. As shown in FIG. 3c, the pulse P is generated only during the period of an odd field, and the rising point of the pulse P coincides with the starting point of the vertical blanking period. As described above, the pulse width of the pulse P between its rising point and its falling point varies (increases or decreases) in accordance with the output level of the CCD 33 as indicated by an arrow 53 in FIG. 3c.

The aforesaid pulse mixer 52 is supplied with the pulse GP of the timing pulse generator 51 and the pulse P of the PWM circuit 38. As shown in FIG. 3d, the OR gate output of the pulse mixer 52 is transferred through the cable 54 and applied to the readout gate 43 of the CCD 33. In this embodiment, by way of example, the CCD 33 is of a type which is provided with an independent readout gate input. There is an alternative type of CCD in which a readout gate signal is superimposed on a vertical transfer pulse for the purpose of charge transfer. This type of CCD is also applicable to the present invention if a signal processing similar to that performed in the embodiment is carried out prior to superimposition.

As shown in FIG. 1, a vertical transfer pulse generator 55 and a horizontal transfer pulse generator 56 are accommodated in the body 23. The timing pulse generator 51 or oscillators 59 and 60 are adapted to input triggering pulses to the pulse generators 55 and 56 through switches 57 and 58, respectively.

Normally (that is, in an operating mode with a shutter function), each of the switches 57 and 58 is switched to a contact a, and the pulse generators 55 and 56 are triggered by transfer signals supplied from the timing pulse generator 15 to perform a common readout operation.

More specifically, a vertical transfer signal generated by the timing pulse generator 51 is input to the vertical transfer pulse generator 55, and the frequency of the vertical transfer signal is 15.75 KHz in accord with the NTSC system. Also, a horizontal transfer signal generated by the timing pulse generator 51 is input to the horizontal transfer pulse generator 56. Although determined by the number of pixels per horizontal row, the frequency of the horizontal transfer signal is 7 MHz in this embodiment.

Each of the switches 57 and 58 is switched between its contacts a and b by the output pulses of the PWM circuit 38. If the output pulse goes to its high level, the switches 57 and 58 are switched so that their respective contacts b are selected. In this case, the oscillated signal outputs of the respective oscillators 59 and 60 are input to the corresponding contacts b.

In a readout mode which has the shutter function to perform a readout operation in response to the output signals of the oscillators 59 and 60 (hereinafter referred to as the "readout mode with shutter function" or the "special mode"), the charges stored in the photosensitive portions (or photodiodes) 41 are removed by a high-speed readout employing a high frequency generated by the oscillators 59 and 60, and thus the storage time (which will subsequently be required for an image to be actually displayed) is controlled.

Such a special mode can be switched on and off under the control of a mode selecting switch 61 which is provided on the scope 22 or the body 23. Therefore, if the switch 61 is switched on to apply an operation control signal to the PWM circuit 38, the special mode can be selected, while, if the switched 61 is switched off, only a normal mode operates.

As described above, in the case of the high-speed readout, the readout gate 43 of the CCD 33 is switched on and the output of each of the photodiodes 41 is supplied to the adjacent vertical transfer CCD 42. In this case, however, the charges stored in the photodiodes 41 may overflow into the corresponding vertical transfer CCDs 42. Therefore, it is preferable for the transfer speed of each of the vertical transfer CCDs 42 to be made some tens of times as high as the transfer speed used in the normal mode. Furthermore, if charges are transferred from the vertical transfer CCDs 42 to the horizontal transfer CCDs 46 at such high speed, the transferred charges may likewise overflow in the horizontal transfer CCDs 46. In order to prevent such overflow, it is necessary to enhance the transfer speed of the horizontal transfer CCDs 46 to a level several to some tens of times as high as the transfer speed used in the normal mode. For these reasons, the oscillators 59 and 60 are provided for the purpose of performing the high-speed transfer of charges.

For example, the oscillator 59 serves to increase the transfer speed of the vertical transfer CCDs 42 to 150 KHz which is about ten times 15.75 KHz in the normal mode. Simultaneously, the oscillator 60 serves to increase the transfer speed of the horizontal transfer CCDs 46 to, in this embodiment, 21 MHz which is about three times 7 MHz in the normal mode. The switches 57 and 58 are interlockingly switched and, when they are connected to the respective contacts b, high-speed transfer is achieved.

FIGS. 3e and 3f respectively show the horizontal transfer pulse output of the horizontal transfer pulse oscillator 56 and the vertical transfer pulse output of the vertical transfer pulse oscillator 55. The horizontal transfer pulse and the vertical transfer pulse are transferred over the cables 62 and 63, respectively, and applied to the CCD 33.

In each of FIGS. 3e and 3f, inclined lines represent the horizontal transfer pulse portion and the vertical transfer pulse portion during the period of an even field. These pulse portions correspond to a normal readout clock frequency (in this embodiment, 7 MHz and 15.75 KHz, respectively). The odd field period shown in each of FIGS. 3e and 3f is the period which it takes until the charges stored for a period longer than a short charge storage time is removed by high-speed transfer.

The even field period shown in each of FIGS. 3a to 3f corresponds to the normal mode and, in this embodiment, during the even field period, the normal-mode operation is executed irrespective of the presence or absence of the shutter function. Incidentally, in the normal mode in which the special mode is not executed, the operation in the odd field is identical with the operation in the even field.

If the readout mode with shutter function is selected, as shown in FIGS. 3a to 3f, high-speed readout (high-speed transfer) of charges and short-time charge storage are executed during the odd field and, during the even field, the charges stored as the result of the aforesaid short-time charge storage are read out by charge transfer in the normal mode. Therefore, during a high-speed readout period 64 in the odd field shown in FIG. 3e, the charges stored in the photodiodes 41 are read out at high speed so that the charges are removed. During the remaining short period 65 which follows the high-speed readout period 64, since neither horizontal transfer pulses nor vertical transfer pulses are supplied, charges are stored in the photodiodes 41. This period 65 is a period equivalent to a shutter velocity or a substantial imaging period (or storage time) and, as the period 65 becomes shorter, the shutter velocity increases. The charges stored during the period 65 are transferred to the vertical transfer CCDs 42 in response to corresponding charge transfer pulses. During the succeeding even field period, the charges are output as a video signal 66 as shown in FIG. 3a.

The period of generation of the output pulse of the PWM circuit 38 varies in accordance with the video signal level of the output signal of the CCD 33. In this embodiment, as such a level increases, the output pulse width increases and therefore the storage time 64 becomes short. As described previously, shortening of the storage time naturally involves a decrease in sensitivity. In this embodiment, however, if the shutter function is performed, the shutter velocity is varied in accordance with the level of a video signal and the storage time is automatically controlled so that a fixed sensitivity which is at or near its optimum level can be obtained, irrespective of the shutter velocity.

In other words, as the CCD output increases, the storage time is shortened and the shutter velocity is increased. Conversely, as the CCD output decreases, the storage time is prolonged and the shutter velocity is decreased, whereby a remarkable decrease in sensitivity is prevented. In this embodiment, as shown in FIG. 3a, if the shutter function is switched on, a video signal is generated during each even field only, but no video signal during each odd field. In this state, it is impossible to view an image on a monitor or the like. In this embodiment, therefore, the video signal generated during each even field period is temporarily stored in a video memory in the video processor 36, and the video signal stored in this even field period is read out during the even field and displayed on the monitor.

Figure 4:
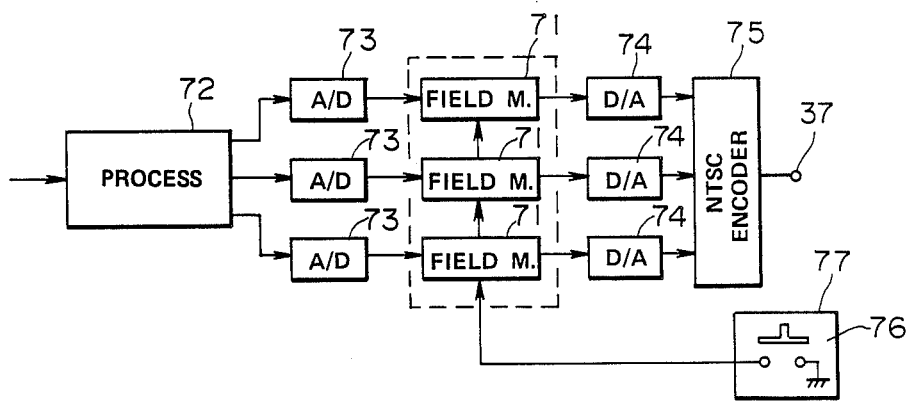
FIG. 4 is a block diagram illustrating the freeze function and its peripheral portion of the first embodiment.

A field memory 71 such as that shown in FIG. 4 may be used as the above-described video memory.

The output signal of the CCD 33 is converted into a Y signal, a R−Y signal and a B−Y signal by a processing circuit 72 disposed in the video processor 36. The signals thus obtained are passed through respective A/D converters 73 and stored in corresponding field memories (freeze memories) 71. The video signal data which has thus been stored in each of the field memories 71 is read out during the next even field period and passed through a corresponding D/A converter 74. Then, the data is converted into a video signal according to the NTSC system by an NTSC encoder 75 and supplied from an output terminal 37 to the monitor.

It is to be noted that the processing circuit 72 may be a circuit of the type that outputs R, G and B signals.

Writing to the respective freeze memories 71 can be stopped by operating a freeze switch 76. Each of the freeze memories 71 is adapted to hold the video signal data which was written immediately before the operation of the switch 76 and to read out such video data for the purpose of providing a display of a still picture.

Figure 5:
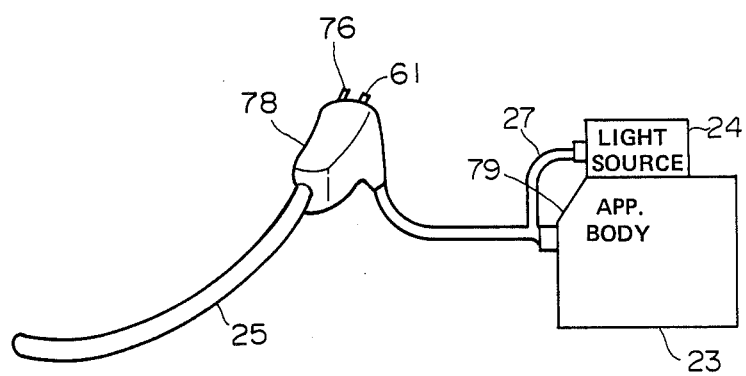
FIG. 5 is a schematic perspective view illustrating an example of the layout of a freeze switch on a video endoscope according to the first embodiment.

It is to be noted that a switch mounting location 77 which defines a position at which the freeze switch 76 is disposed is provided on, for example, an operating section 78 of the scope 22 as shown in FIG. 5 (or an operating panel 79 of the body 23).

In the case of imaging using the shutter function described above, its primary purpose is to make it possible to freeze and observe the obtained image or take a photograph of the frozen picture as well as to display the image on a monitor at real time. When the freeze switch 76 is switched on, the output of the field memory 71 is frozen and the resultant frozen picture is displayed on the monitor. An operator can manually operate the freeze switch 76 at a desired timing so as to obtain a frozen picture. It is very useful in the efficiency of diagnosis that the freeze switch 76 is provided on the operating section of the scope 22.

In general, if a mounting location 80 at which the mode selecting switch 61 is located for switching on and off the shutter function described above is provided on the operating section 78 as shown in FIG. 5, the scope 22 and the body 23 are connected by a cable as long as several meters and the body 23 can be disposed at a remote location so as not to preclude the diagnosis of a doctor. Such an arrangement, therefore, is remarkably useful for the doctor who must manipulate the scope 22.

In accordance with the first embodiment described above, it is possible to perform imaging and observation in a common way and also to provide an observation image which is scarcely blurred, by selecting a charge storage time shorter than that of the normal mode. If it is desired to obtain an image free from blur, for example, in order to observe an object which is moving, the mode selecting switch 61 is operated to cause the PWM circuit 38 to output a pulse whose pulse width has been modulated to a pulse width according to the video-signal level output from the video-signal-level detector 35. This video-signal level is used to remove the charges which were stored prior to the period (shown as 65 in FIG. 3) suitable for charge storage. More specifically, the readout gate 43 of the CCD 33 is opened, the high-frequency oscillated signals of the oscillators 59 and 60 are respectively applied to the vertical transfer pulse generator 55 and the horizontal transfer pulse generator 56, and the charges stored in the photosensitive portions 41 are removed by high-speed transfer pulses. Subsequently, substantial charge storage (involving no removal of charges) is executed. After this optimum imaging period has passed, a gate pulse is applied to the front edge of the vertical blanking period of the odd field, and the charges stored in the photosensitive portion 41 are transferred in the vertical and horizontal directions by drive pulses output from the timing pulse generator 51 similarly to that of the normal operation mode. The resultant video signal is output to the video processor 36. The video processor 36 converts the signal into a normal video signal (according to the NTSC system or the like) and outputs it to the monitor. Accordingly, a sharp image which is scarcely blurred can be displayed on the monitor. Furthermore, it is possible to display an image which is so bright as to enable rapid diagnosis.

Figure 6:
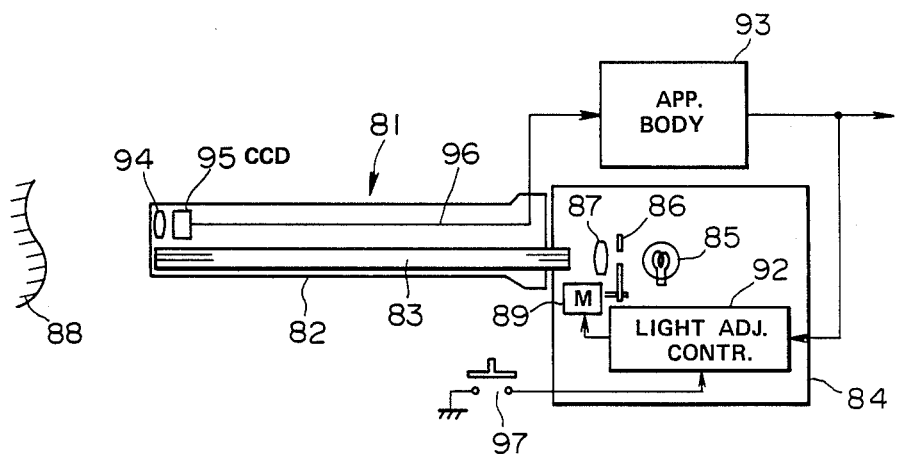
FIG. 6 is a block diagram of a second embodiment of the present invention.

FIG. 6 shows a second embodiment of the present invention.

In the second embodiment, there is provided a video endoscope apparatus provided with automatic light adjusting means. This video endoscope apparatus is adapted to perform automatic light adjustment in its normal mode and to perform no automatic light adjustment in its special mode which causes the shutter function to operate.

A light guide 83 is inserted through an inserting section 83 of an electronic scope 81, and the trailing end of the light guide 83 can be connected to a light source device 84.

A beam of light emitted from a lamp 85 in the light source device 84 is propagated past a movable light shielding member 86, converged by a lens 87, introduced into the light guide 83, and transferred through the light guide 84. The light is projected onto an object 88 from the leading end of the light guide 84.

As shown in FIG. 7, the movable light shielding member 86 can be rotated by a DC motor 89 in the direction indicated by an arrow 91 so as to shield a light beam to be incident upon an entrance end surface 83A of the light guide 83. The DC motor 89 is reversibly activated under the control of a light adjustment control circuit 92. The light adjustment control circuit 92 receives the video signal passed through a video processor in a body 93, detects the video signal, then detects the level of the video signal, and then compares this level with a reference level. If the level of the video signal varies with respect to the reference level, the movable light shielding member 86 is rotated by the motor 86 in the direction in which the member 86 shields the light beam or in the opposite direction and is thus controlled so that the varying level of the video signal may approach the reference level.

As illustrated, the leading end of the inserting section 82 is provided with an objective lens 94 and a CCD 95 disposed in a focal plane of the objective lens 94. As in the first embodiment, although not shown, the CCD 95 can be supplied with a drive signal for driving it in either its normal or special mode. The CCD 95 outputs a signal by the application of the drive signal, and the output signal is input to the body 93 through a cable 96.

In the second embodiment, a mode selecting switch 97 is connected to the light adjustment control terminal of the light adjustment control circuit 92. For example, if the mode selecting switch 97 is switched on, that is, if the special mode in which the shutter function is operated is selected, the light adjustment control circuit 92 stops the operation of its light adjustment control function and causes the movable light shielding member 86 to rotate counterclockwise as viewed in FIG. 7 and maintains it in a state in which the member 86 does not shield the light from the lamp 83. This state corresponds to the fully opened state of an aperture (or iris).

Since the quantity of illuminating light reaches a maximum when the shutter function is switched on, it is possible to shorten the storage time without sacrificing sensitivity. Accordingly, an image which is improved in sharpness can be obtained from an object which is moving.

FIG. 8 shows the essential portion of a third embodiment of the present invention.

The third embodiment is adapted to produce a flash of light when its shutter function is switched on.

A lamp 101 in this embodiment is arranged such that the quantity of light emitted therefrom varies in proportion to an applied voltage. If the lamp 101 is used in its normal mode in which the shutter function is off, the voltage V1 of an electrical power source 102 is applied to the lamp 101 through a diode 103. Another electrical power source 104 is an electrical power source used for producing a flash of light. In this embodiment, the voltage V2 of the electrical power source 104 is set to a level two times as high as the voltage V1 of the electrical power source 102. The output of the electrical power source 104 is applied to the lamp 101 through a switch 105 and a diode 106. Incidentally, the diodes 103 and 106 serve to prevent interference from occurring between the electrical power sources 102 and 104.

The switch 105 is switched on by the output of a flash pulse generator 107 to cause the lamp 101 to generate a flash of light. The lightening-flash pulse output from the flash pulse generator 107 has the signal waveform shown in FIG. 9c, and this signal waveform is obtained by passing a vertical synchronizing signal (shown in FIG. 9a) and the output signal (shown in FIG. 9b) of the PWM circuit 38 through an AND circuit (not shown). The lamp 101 generates a flash of light during a period (indicated at 109 in FIG. 9c) for which the lightening-flash pulse is kept at its high level. (In this embodiment, the quantity of light produced by flashing is two times the quantity of light produced by normal emission.)

As described previously, when the shutter function is switched on, the quantity of light emitted from the light source lamp 101 is intensified to project an increased quantity of light onto an object. It is possible, therefore, to obtain a sharp image at high shutter velocities without decreasing sensitivity. In general, since a light guide in a generally available type of scope is constituted by a limited number of optical elements, the quantity of light incident upon the light guide is restricted. For this reason, if light of great energy is incident upon such a light guide, a portion of the light energy is converted into thermal energy, with the result that the entrance end of the light guide may burn. However, since the lamp is flashed, it is possible to prevent burning effectively.

Figure 10:
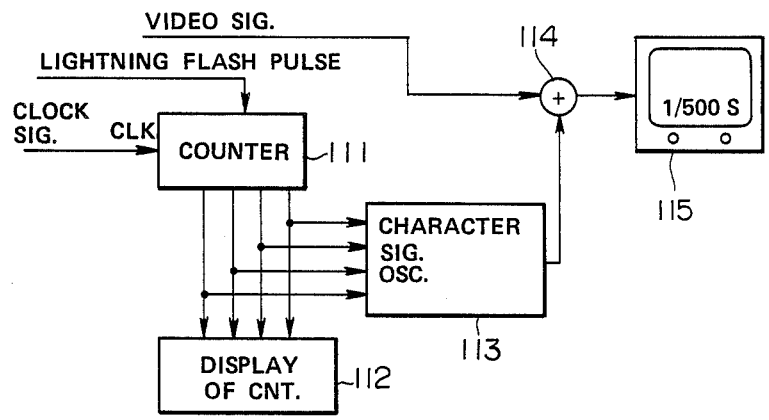
FIG. 10 is a block diagram showing the essential portion of a fourth embodiment of the present invention.

FIG. 10 shows the primary portion of a fourth embodiment of the present invention.

The fourth embodiment is arranged such that, when the shutter function is switched on, its shutter velocity superimposed on a video signal is displayed on the monitor.

A counter 111 receives clock signals CLK and counts the number thereof. The lightening-flash pulse shown in FIG. 9c is applied to a reset terminal of the counter 111, and the counter 111 is reset by the falling edge of this pulse.

Accordingly, the count of the counter 111 immediately before resetting is stored as its final count in a register (not shown) in the counter 111. The output of the register is input to a count display 112, and the shutter velocity is displayed on a digital display. The display 112 may be provided on the operating panel of either the body or the scope. The count displayed can be made coincident with the shutter velocity by suitably selecting the frequency of a clock signal.

The output of the counter 112 is input to a character signal generator 113 and characters which represent a shutter velocity corresponding to the count are read out in synchronization with a synchronizing signal. The characters thus read are mixed with a video signal by a mixer 114 and displayed at a corner of the display screen of an observing monitor 115.

In accordance with the fourth embodiment, if the shutter function is switched on, the shutter velocity varies in accordance with the conditions of an object (for example, the distance to the object or the intensity of reflection of the object). However, since an operator can readily confirm the shutter velocity while actually using the endoscope apparatus, he can predict to what extent each shutter velocity varies the quality of an image which will be obtained. This is useful in diagnosis. When photographs are to be taken by using a fiber scope, such information about shutter velocities is useful.

Figure 11:
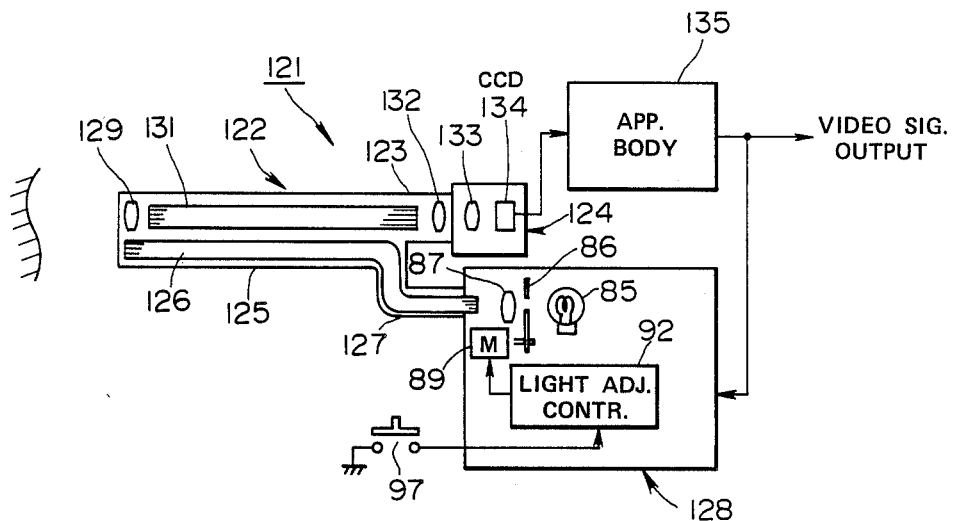
FIG. 11 is a block diagram of a fifth embodiment of the present invention.

FIG. 11 shows the primary portion of a fifth embodiment of the present invention. In a video endoscope apparatus 121 according to the fifth embodiment, a television camera 124 can be detachably mounted to an eyepiece portion 123 of a fiber scope 122.

The leading end of an inserting section 125 of the fiber scope 122 is provided with an objective lens 129, and an image guide 131 is inserted through the inserting section 125 in such a manner that the entrance end of the image guide 131 faces the focal plane of the objective lens 129. An optical image of an object is transferred through the image guide 131 from its leading end to its trailing end so that the image can be observed on an enlarged scale through an eyepiece lens 132. If a television camera 124 is attached to the eyepiece portion 123, such an optical image can be formed on a CCD 134 by a focusing lens 133. Although not shown, drive signals can be applied to the CCD 134 so that imaging in the normal mode and imaging in the special mode can be selectively performed as described previously in connection with FIG. 1. The signal read out of the CCD 134 is input to a body 135, and a video signal is output from the body 135.

The fifth embodiment is a modified version of the second embodiment shown in FIG. 6 in that the electronic scope 81 is replaced with the television camera 124 which includes both a fiber scope 122 and the CCD 134. The effects and advantages of the fifth embodiment are, therefore, similar to those of the second embodiment. In addition, the fifth embodiment can advantageously be applied to a conventional type of fiber scope.

Figure 12:
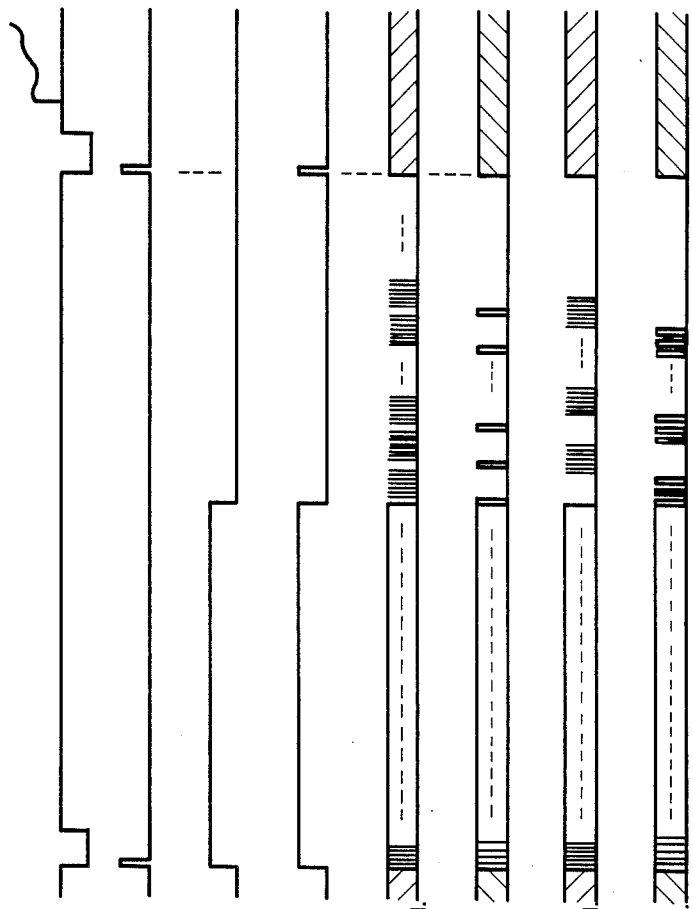
FIGS. 12a to 12g, 12f' and 12g' are timing charts which serve to illustrate the operation of a sixth embodiment of the present invention.

It is to be noted that, in the first embodiment described above, if unwanted charges are to be removed, the vertical and horizontal transfer signals are supplied during the time 64 for which pulses are output from the PWM circuit 18 as shown in FIGS. 3e and 3f. However, as shown in FIGS. 12f and 12g or 12f' and 12g', the CCD 13 may be operated so that the charges in all the pixels thereof may be removed at the end of the time 64. Since the amount of charge stored in this case is small, a single vertical transfer pulse may be applied to the CCD 13 and then horizontal transfer pulses equivalent in number to the horizontal rows of the pixels may be supplied to the same as shown in FIGS. 12f and 12g. Alternatively, as shown in FIGS. 12f' and 12g', after some or more vertical transfer pulses have been continuously supplied, horizontal transfer pulses equivalent in number to the horizontal rows of the pixels may be supplied so as to remove the charges in a short time without overflow of the charges. FIGS. 12a, 12b, 12c and 12d are views similar to FIGS. 3a, 3b, 3c and 3d except that they differ from each other in time scale only and therefore their description is omitted.

As described above, in each of the first to sixth embodiments of the present invention, there has been provided means for removing the charges stored for the period other than the desired charge storage time. It is possible, therefore, to obtain an image of sufficient sharpness even when an object is moving.

A seventh embodiment of the present invention will be described below with reference to FIGS. 13 to 21.

Figure 13:
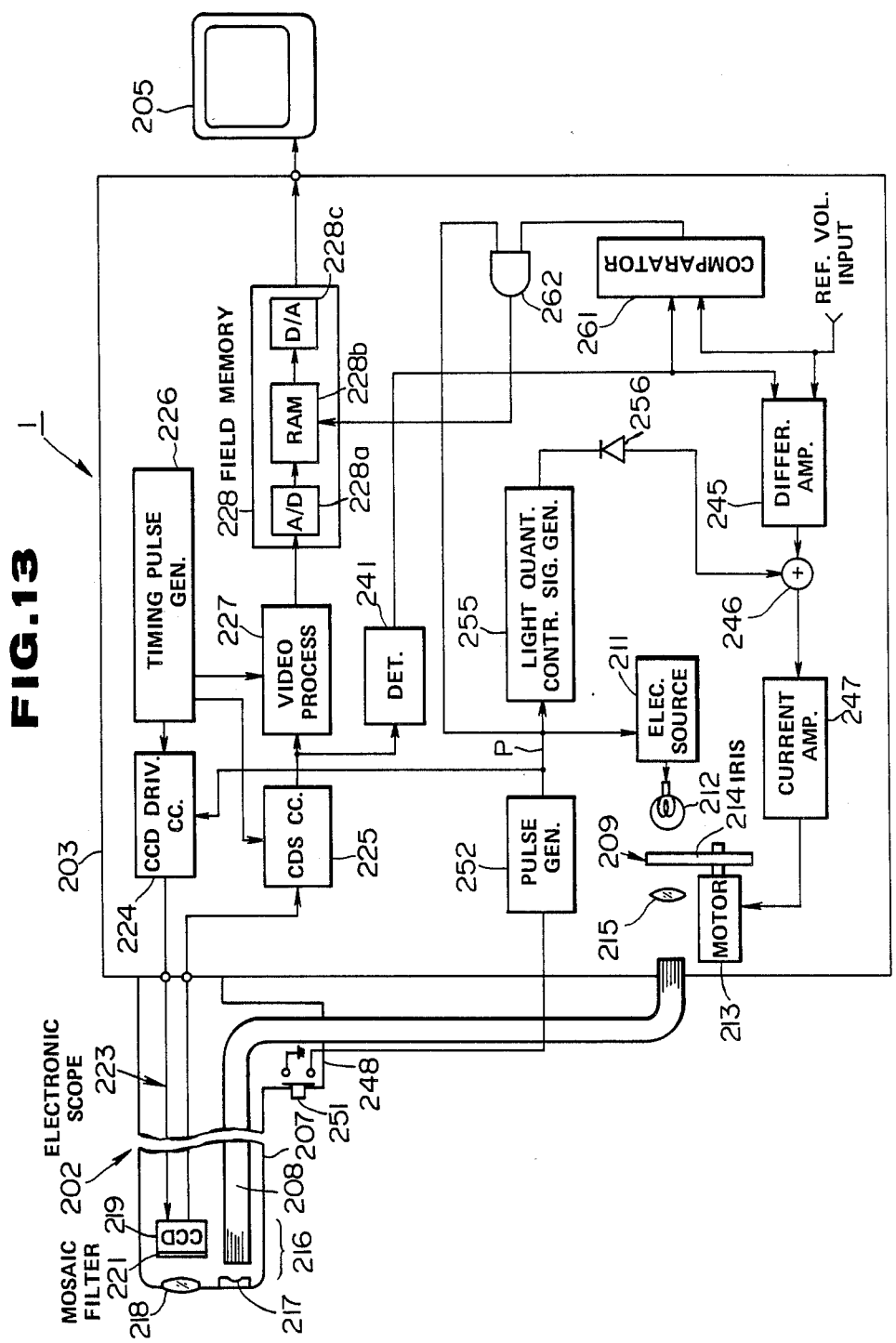
FIG. 13 is a block diagram of a video endoscope apparatus according to a seventh embodiment of the present invention.

As shown in FIG. 13, a video endoscope 201 according to the seventh embodiment includes an electronic scope 202, a signal processing device 203 which accommodates signal processing means associated with the electronic scope 202 and light source means, and a color monitor 205 for providing a display of the video signal output from an output terminal 204 of the signal processing device 203. The electronic scope 202 has an elongated inserting section 207 which can be inserted into a body organ or the like, and a light guide 208 for transmitting illuminating light is inserted through the inserting section 207. The entrance end of the light guide 208 is attached to a connector receptacle of a light source device 209, whereby the illuminating light is supplied.

In the light source device 209, a white light lamp 212 such as a xenon lamp receives electric power supplied from a light source 211 to emit white light, and the white light is passed through a light adjustment member 214 which is rotated by a motor 213, so that the quantity of transmitted light can be varied. The white light which has passed through the light adjustment member 214 is converged by a condenser lens 215 and projected onto the entrance end of the light guide 208.

The illuminating light transmitted through the light guide 208 passes through the exit end thereof which is fixed at a leading end of the inserting section 207, and is, in turn, projected toward an object by a projection lens 217. An image of the object thus illuminated is focused on a CCD 219 by an objective lens 218 disposed at the leading end 216, the CCD 219 being disposed at the focal plane of the objective lens 218. A color compensating mosaic filter 221 (in which color compensating filter pieces are arranged in a mosaic form) is attached to the photosensitive surface of the CCD 219.

A CCD driving circuit 224 supplies a horizontal transfer pulse $\phi H$, a reset pulse $\phi$ and a vertical transfer pulse $\phi$ to the CCD 219 through a signal cable harness 223. Thus, the CCD 219 outputs a photoelectrically converted signal and transfers it through the signal cable harness 223 to a correlation double sampling circuit 225 (hereinafter referred to as "CDS circuit 225"). The signal is subjected to double sampling so that $1/f$ noise derived from the CCD 219 is suppressed. Sampling pulses for the CDS circuit 225 are supplied from a timing pulse generator 226, and sampling is performed with respect to each pixel. The output of the CDS circuit 225 is input to a video processing circuit 227, converted into, for example, an NTSC composite video signal, and supplied to a field memory 228. The field memory 228 is constituted by, for example, an A/D converter 228a, a RAM 228b having a capacity (of n bits) corresponding to one field, and a D/A converter 228c.

Figure 14:
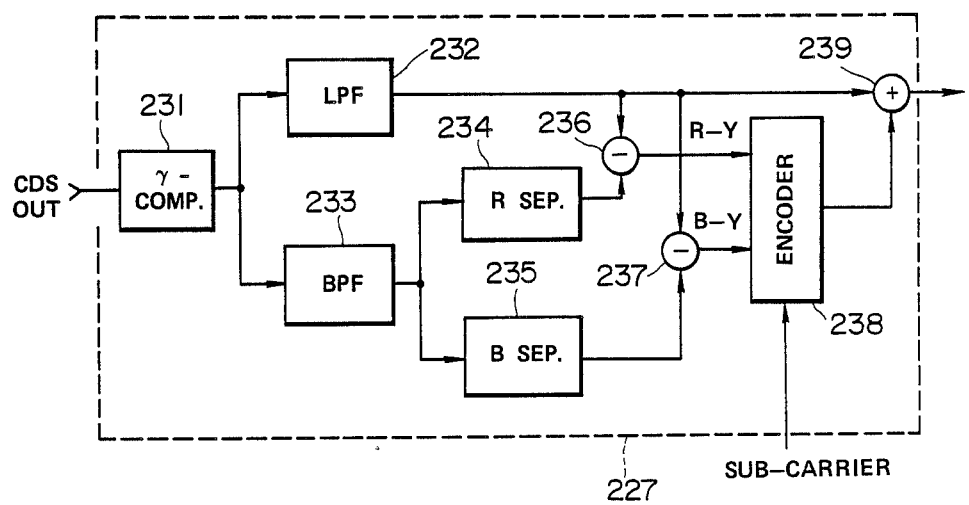
FIG. 14 is a circuit diagram of a video processing circuit for use in the video endoscope apparatus according to the seventh embodiment.

FIG. 14 shows a concrete example of the construction of the above-described video processing circuit 227.

The output signal of the CDS circuit 225 contains luminance signal components and color signal components. The CDS output signal is input to a $\gamma$ correction circuit 231, in which its $\gamma$ characteristic has been converted to approximately 0.45. Then, the signal is input to a low-pass filter 232 (hereinafter referred to as the "LPF 232") and a band-pass filter 233 (hereinafter referred to as the "BPF 233"). In this embodiment, since the color compensating mosaic filter 221 is used, the CCD 219 generates a luminance signal as a baseband and a chrominance signal as a carrier wave.

Figure 15:
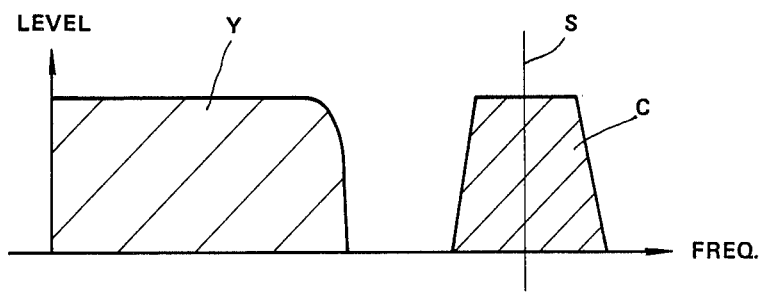
FIG. 15 illustrates the spectrum of the signal band of a signal which is input to the video processing circuit according to the seventh embodiment.

FIG. 15 shows the spectrum of the output signal of the CCD 219. In this figure, Y represents the luminance signal component obtained as a baseband, S represents a carrier signal for the chrominance signal components, and C represents the sideband of the chrominance signal components. The luminance signal is extracted by the LPF 232 whose cutoff frequency is a frequency located between the band of the signal Y and that of the signal C, while S and C (a chrominance carrier) is extracted by the BPF 233. The chrominance carrier extracted by the BPF 233 is supplied to an R separator 234 and a B separator 235. The R separator 234 separates an R signal (red signal) from the chrominance carrier, while the B separator 235 separates a B signal (blue signal) from the same. The R signal separated by the R separator 234 is applied to one input of a difference circuit (substraction circuit) 236, while the B signal separated by the B separator 235 is applied to one input of another difference circuit (substraction circuit) 237. The luminance signal Y is input to the other inputs of the respective R and B separators 234 and 235. Thus, the luminance signal Y is subtracted from each of the R and B signals, and the difference circuits 236 and 237 output color-difference signals R−Y and B−Y, respectively.

Both the color-difference signals R−Y and B−Y are input to a color encoder circuit 238 and are used as modulating inputs of an orthogonal modulator using a sub-carrier. The color encoder circuit 238 outputs a chroma signal and supplies it to one input of a mixer 239. The chroma signal is mixed with the luminance signal Y suppled to the other input of the mixer 239. The mixer 239 outputs, for example, an NTSC composite video signal.

The output signal of the CDS circuit 225 shown in FIG. 13 is input to the video processing circuit 227 and a detector 241. In the detector 241, the signal is subjected to detection employing its mean level or its peak level and converted into a DC signal. The mean level or the peak level may be arbitrarily selected in accordance with the conditions of an object and, in this embodiment, mean-value detection is employed for the purpose of illustration only. Therefore, the detector 241 outputs a DC signal of magnitude proportional to the level of the photoelectrically converted output of the CCD 291.

Referring to FIG. 16 by way of example, a solid line represents a signal output from the CDS circuit 225 and a dashed line represents a DC voltage level 42 which is detected with its mean value and which becomes a signal output from the detector 241. Incidentally, $E_0$ denotes the maximum level. As a matter of course, he output level of the detector 241 varies in accordance with the level of the photoelectrically converted output of the CCD 219.

Also, the level of the photoelectrically converted output of the CCD 219 varies in accordance with the intensity of illumination. In this embodiment, means is provided for increasing the quantity of illuminating light by means of the light adjustment member shown in FIG. 17. FIG. 17 is a schematic view, taken in the direction of the axis of the illuminating light, of the light adjustment member 214 and a peripheral portion thereof.

The light adjustment member 214 has an arm 214A attached to the rotary shaft of a motor 213, and is capable of rotating in either of the directions indicated by an arrow A in accordance with the direction of rotation of the rotary shaft of the motor 213. The light adjustment member 214 has a disk-shaped light shielding portion provided with a cutout. Therefore, the portion of a light beam 243 that faces the cutout is allowed to proceed toward the condenser lens 215, but the other portion that opposes the disk-shaped light shielding portion other than the cutout is shielded.

For example, the state shown by a solid line in FIG. 17 is a fully open state in which the light beam 243 is passed substantially completely, while, in the state shown by a dashed line, the quantity of illuminating light is significantly reduced. It is possible, therefore, to adjust the quantity of illuminating light projected onto an object by reversibly controlling the rotation of the light adjustment member 214. As will be described later, in a normal imaging mode, the light adjustment member 214 is placed under automatic light adjustment control and is generally held in a state wherein it is not fully open. In the special mode in which imaging is performed in a short storage time, the light adjustment member 214 is controlled to gradually open toward its full-open position. It is determined whether or not the level of an image signal obtained during such light adjustment has reached a predetermined level. When the predetermined level is reached, the image signal is held in the field memory 228.

The output signal of the aforesaid detector 241 is applied to one input terminal of a differential amplifier 245, and a reference voltage Es is applied to the other input of the differential amplifier 245. The voltage value of the reference voltage Es is set to a voltage approximately equal to the output level of the detector 241 when a video signal output reaches a proper level. That is, such a voltage value is used as a reference level for automatic light adjustment. The output of the differential amplifier 245 is input to a current amplifier 247 via a mixer 246 and subjected to current amplification so that the DC reversible motor 213 may be driven. In this manner, a control loop for effecting automatic light adjustment is constituted, and the amount of rotation of the light adjustment member 214 is reversibly controlled by the control loop for automatic light adjustment so that the output voltage of the detector 241 may equal the reference voltage Es.

An operating section 248 of the electronic scope 202 is provided with a switch 251 for selecting a special imaging mode in which imaging is effected by switching the storage time (exposure time) from normal 1/60 seconds to one tenth thereof, i.e. 1/600 seconds. When the switch 251 is switched on, a trigger signal is input to a pulse generator 252. Therefore, when the switch 251 is depressed, the pulse generator 252 outputs a pulse.

In this embodiment, as shown in, for example, FIG. 18a, when depressed, the switch 251 outputs a trigger pulse and, as shown in FIG. 18b, the pulse generator 252 responds to the trigger pulse to output a pulse P of duration equivalent to ten fields (or 1/6 seconds).

The output pulse P of the pulse generator 252 is input to a CCD driving circuit 224. If the pulse P is high, the CCD driving circuit 224 reads out a signal which has been stored in the CCD 219 for one tenth of the normal storage time. As described previously, this embodiment is provided with the control means for automatic light adjustment. Therefore, when the special imaging mode is selected by depressing the switch 251, the storage time is shortened to one tenth of the normal storage time and thereby the output level of the CCD 219 is reduced to about one tenth of its normal output level. Thus, the light adjustment member 214 is rotated by its automatic light adjustment function in the direction in which it fully opens.

However, it takes a certain time period to follow the automatic light adjustment control and, in practice, a follow-up time period which is a maximum of one second is needed. Therefore, in the case of the above-described pulse P of duration equivalent to ten fields, the output, shown in FIG. 19b, of the CDS circuit 225 is obtained by the control means for automatic light adjustment.

More specifically, in the normal imaging mode shown on the left side of each of FIGS. 19a, 19b and 19c, the output signal of the CDS circuit 225 is at its proper level. At the timing shown as time t1, the switch 251 is switched on and, as shown in FIG. 19a, the pulse generator 252 outputs the pulse P. Simultaneously, the level of the photoelectrically converted output is reduced to one tenth of its normal level and, as shown in FIG. 19b, for the period which follows time t1 and for which the pulse P is being output, the level of the output signal of the CDS circuit 225 falls from the level (denoted by V1) prior to time t1 to about one tenth thereof (denoted by V2). As described above, the automatic light adjustment control does not instantaneously follow, and the output of the detector 241 slowly rises by automatic light adjustment as shown in FIG. 19c, but only slightly rises for a period as long as 1/6 seconds (in FIG. 19, ΔV denotes the value of this rise).

For this reason, this embodiment is provided with the following means capable of forming a frozen picture free from blurs even when the storage time is as long as 1/6 seconds.

The output of the pulse generator-252 is input to a light-quantity control signal generator 255, and this signal generator 255 generates a single sawtooth wave (slope wave). The sawtooth wave is applied through a diode 256 to the other input terminal of the mixer 246, superimposed on the output signal of the differential amplifier 245, and input to the current amplifier 247. The motor 213 is activated by the sawtooth wave to force the light adjustment member 214 to open, thereby increasing the quantity of illuminating light.

As shown in FIG. 20a, when triggered by the pulse P from the pulse generator 252, the light quantity control signal generator 255 outputs a sawtooth wave such as that shown in FIG. 20b. The voltage level of this sawtooth wave is set so that its initial value $E_H$ may be higher than the maximum value of the output voltage of the differential amplifier 245, with its final minimum value $E_L$ exceeding the minimum output value of the detector 241.

The sawtooth wave generated is passed through the diode 256 and mixed with the output of the differential amplifier 245 in the mixer 246 to provide a mixed waveform such as that shown in FIG. 20c. As illustrated, symbol $E_R$ represents the output voltage of the differential amplifier 245 during the operation of automatic light adjustment. When the pulse P is output, the sawtooth wave is superimposed on that output voltage to form a voltage waveform which slopes downwardly. Finally, the level of the output voltage reaches $E_{RL}$, at which time the light adjustment member 214 does not at all shield the light beam, that is, opens fully as shown by the solid line in FIG. 17. Accordingly, the maximum quantity of illuminating light is projected onto an object. Conversely, if the output voltage of the differential amplifier 245 is higher than $E_R$, the light adjustment member 14 is moved to a position at which the light beam is completely shielded. The middle potential ($E_H - E_L$)/2, shown in FIG. 20b, of the sawtooth wave is set to be approximately equal to the automatic light adjustment operating voltage $E_R$. Incidentally, the diode 256 serves to prevent the initial value $E_H$ of the sawtooth wave from affecting the output $E_R$ of the differential amplifier 245. The potential of $E_R$ varies with time in accordance with the conditions of the object and, therefore, the difference between $E_H$ and $E_L$ is greater than the output range of the differential amplifier 245. Accordingly, at the same that the storage time switches from 1/60 to 1/600 seconds, the quantity of illuminating light projected on a subject is forcibly varied toward its maximum in accordance with the control voltage shown in FIG. 20c. While the quantity of illuminating light projected on the subject is being increased toward the maximum, the detector 214 detacts the mean level of input signals. When the mean level reaches a proper value, the video signals obtained by imaging in the succeeding field are read into the field memory 228, whereby a frozen picture is obtained in the special imaging mode.

Accordingly, the output signal of the detector 241 is supplied to one input terminal of a comparator 261, while the reference voltage $E_S$ equivalent to the proper level is applied to the other input terminal of the comparator 261. The comparison output which is generated by the comparator 261 when the level of the former output signal has reached the proper level is supplied to one input of an AND circuit 262 which serves as an AND gate. The output of the pulse generator 252 is applied to the other input terminal of the AND circuit 262. The AND circuit (or AND gate) 262 is opened in response to the pulse of the pulse generator 252. If the comparator 261 outputs a signal (indicating that the output level of the detector 241 has reached the proper level) when the AND gate 262 is open, the signal output is passed through the AND gate 262 and applied to a light control terminal of the filed memory 228. Thus, the field memory 228 stores composite video signals for one field which will be output from the video processing circuit 227 during the succeeding field.

The above-described operation will be described below with reference to FIGS. 21a to 21d.

For example, when the special imaging mode is selected at time t1, the light-quantity-control signal generator 255 outputs a sawtooth wave. The sawtooth wave is mixed with a signal for the normal automatic light adjustment in the mixer 246 to provide a signal of a waveform such as that shown in FIG. 21a. This signal is passed through the current amplifier 247 and applied to the motor 213. The motor 213 is operated in the direction in which the light adjustment member 214 is forced to fully open, thereby increasing the quantity of illuminating light.

Accordingly, as shown in FIG. 21b, the output level of the CDS circuit 225 drops to approximately one tenth thereof at time t1. Subsequently, since the light adjustment member 214 is forced to gradually retract from the optical path, the quantity of illuminating light increases correspondingly and the output level also increases gradually.

As shown in FIG. 21c, the mean level of the output of the detector 241 drops to about one tenth thereof immediately after time t1. However, as the quantity of illuminating light is increased by the light adjustment member 214, the mean value output also increases. The output of the comparator 261 to which the output of the detector 241 is input is initially at its low level as shown in FIG. 21d. At time t2 when the output level of the detector 241 reaches the level of the reference voltage $E_S$, the output of the comparator 261 is switched to its low level. The resultant output is applied to the field memory 228 via the AND gate 262. In consequence, the video signals for the succeeding one field are stored in the field memory 228, and the stored video signals can be displayed on a color monitor 205 in the form of a frozen picture.

With this embodiment, it is possible to instantly obtain frozen-picture signals with proper exposure and free from blurs. In addition, this embodiment has the advantage that the electronic scope 202 having a simple construction and a reduced size can be achieved. Furthermore, this embodiment can be applied to conventional types of electronic scopes without the need to modify its signal processing system.

In this embodiment, for example, a xenon lamp is used as the light source lamp 212. If the voltage applied to the lamp 212 is instantaneously increased (so as to produce a flash of light), it is possible to increase the quantity of emitted light without sacrificing the life of the lamp and to obtain frozen-picture signals at a rapid timing. The output pulse of the pulse generator 252 is input to a electrical electrical power source 211 to utilize the light source to compensate for a decrease in the sensitivity of the CCD 211 when a storage time of 1/600 seconds is selected in the 1/6-second special imaging mode.

It is to be noted that, in the special imaging mode, the light source lamp for the special imagine mode is flashed a plurality of times and the quantity of each flash of light is increased in a stepped manner. When the signal level output from the detector 241 has reached a proper level, video signals corresponding to the relevant flash of light may be stored in the field memory 228. In this case, if the proper level is detected and the charges for one field have been stored, the special imaging mode may be reset. Also, the signal level may be held at a flash-lighting level coincident with the proper level and the output signals may be output to an optical storage means so as to perform high-speed imaging.

Furthermore, in a case where the light source is caused to perform flash lighting, the intensity of emission may be variably controlled by a level detecting means for detecting the quantity of illuminating light immediately before the execution of the special imaging mode and the light source may be caused to emit light which has been intensified up to ten times the detected quantity of illuminating light. With this arrangement, it is possible to provide video signals which are sufficiently high in S/N ratio and which are not blurred even if a video signal is stored in the field memory or the like without necessarily determining whether or not the output level of the detector 241 is the proper level.

Figure 22:
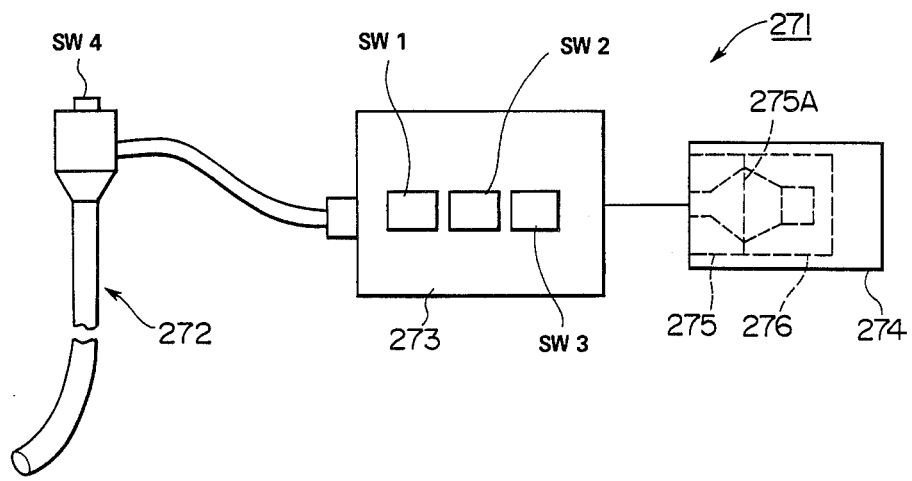
FIG. 22 is a schematic view of the entire arrangement of an eighth embodiment of the present invention.

FIG. 22 schematically shows the external appearance of an eighth embodiment of the present invention.

The eighth embodiment is provided with a device shutter function. The device shutter function can prevent blur which may easily occur when an object at a short distance is imaged, but involves the side effect of deteriorating image quality due to a lowering in sensitivity. The eighth embodiment contemplates the amerioliation of such deterioration of the image quality.

In the video endoscope system 271 shown in FIG. 22, an electronic scope 272 is connected to a signal processing device 273 with a shutter function, and the signal processing device 273 is connected to a recording device 274 so that an image obtained by the electronic scope 272 can be recorded.

In the eighth embodiment, the recording device 274 is constituted by a monitor 275 and a direct-photographing type of camera 276, and the picture displayed on a CRT screen 275A of the monitor 275 can be formed directly on a film in the camera 276. The signal processing device 273 is provided with three switches: a freeze switch SW1, a release switch SW2 and a shutter switch SW3.

If it is particularly desired to diagnose and record a sick portion which moves quickly, the switches SW3 and SW1 are switched on to select a shutter mode and a freeze mode. In such an ON operation, the signal processing system in itself is not switched to the shutter mode nor the freeze mode and only provides a display of standby. This arrangement is intended for improving operability and enabling a desired image to be smoothly photographed.

In general, it is impossible for an operator to immediately locate the leading end of the electronic scope 272 in the vicinity of the desired sick portion. It is necessary, therefore, to gradually move the leading end from a far point toward the sick portion, so that near-point observation is enabled. Accordingly, even in the shutter mode, the deterioration of image quality, particularly the insufficiency of sensitivity is not allowed during observation from a far point.

After the leading end has been located at a near point which can satisfy the demand of the operator, he initiates a recording operation.

For this reason, the signal processing device 273 and the electronic scope 272 are provided with the release switch SW2 and a release switch SW4, respectively. A release mode is selected by operating the switch SW2 or SW4. At this time, the signal processing circuit initiates its shutter operation to enable recording of a frozen picture free from blurs.

Figure 23:
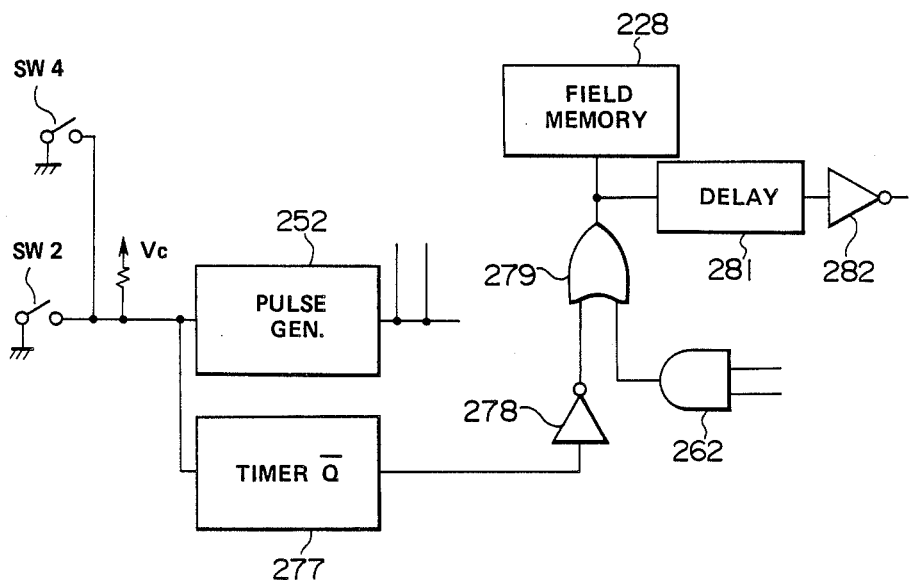
FIG. 23 is a block diagram of the essential portion of the eighth embodiment.

As shown in FIG. 23, the output of the release switch SW2 or SW4 is input to a pulse generator 252 and a timer 277 so as to start the operation of the timer 277. As shown in FIGS. 24a to 24e, at time t1 at which the switch SW2 or SW4 is operated, the progressive opening operation of the light adjustment member 214 is started, and the timer 277 outputs a signal which goes to its low level at time t4 later than time t3 at which the light adjustment member 214 reaches its fully open state.

The output of the timer 277 is supplied to one input of an OR circuit 279 via an inverter 278, while the output signal of an AND circuit 262 is supplied to the other input of the OR circuit 279. After the output of the timer 277 and the output signal of the AND circuit 262 have been ORed by the OR circuit 279, the result is input to the field memory 228 as a write control signal. Also, the output of the OR circuit 279 is input as a release signal to the recording device 274 through a delay device 281 and an inverter 282. The other construction of the eighth embodiment is similar to that of the signal processing circuit of the seventh embodiment shown in FIG. 13.

The operation of the eighth embodiment will be described hereinbelow.

Figure 24:
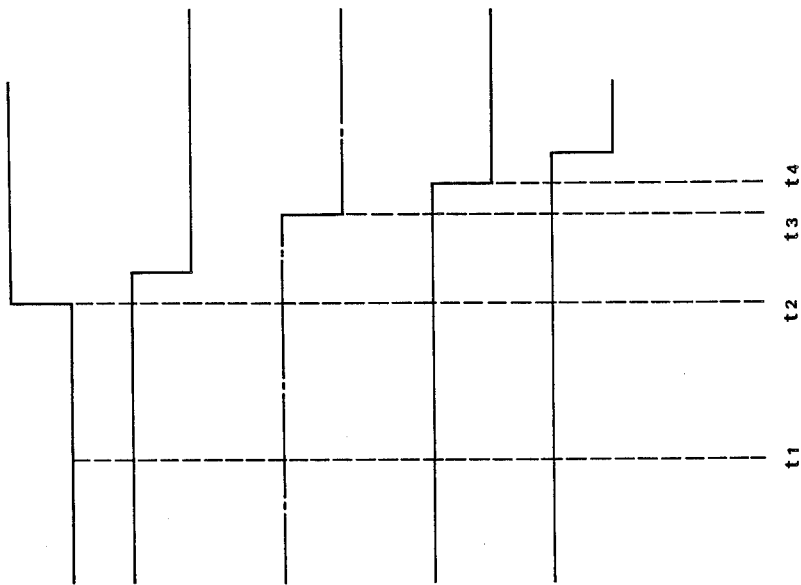
FIGS. 24a to 24e constitute a timing chart illustrating the operation of the eighth embodiment.

In the shutter mode and the freeze mode which are selected by the switches SW3 and SW1, when the release switch SW2 or SW4 is pressed, the video signal level temporarily lowers and thereafter recovers gradually, as described above in connection with the first embodiment. When the video signal level after this release operation coincides with that immediately before the same, as shown in FIG. 21d or 24a, the output of the comparator 261 goes to its high level to cause the entire circuitry to initiate a freeze operation. Thus, the field memory 228 reads video signals for one frame in response to the output of the AND circuit 262, and the resultant frozen picture is displayed on a monitor screen (not shown). Thereafter, the release signal goes to its high level by passing through the delay device 281 and the inverter 282, and a camera 276 effects exposure of one frame in response to the low-level release signal.

In this embodiment, if the video signal level has not yet reached to its proper level after time t3 at which the light adjustment member (or iris) 214 is fully opened as shown in FIG. 24c, the timer 277 operates to effect automatic photography.

For example, if an operator performs a shutter release operation in the shutter mode without noting that an object is positioned at a remote location, the level of video signals may not at all reach an initial level (or proper level). In this case, after the quantity of illuminating light has reached its maximum, the timer 277 operates to effect shutter release operation and photography.

More specifically, after the light adjustment member (or iris) 214 has been fully opened, the output signal of the timer 277 goes to its low level as shown in FIG. 24d, and is supplied to the field memory 228 through the inverter 278 and the OR circuit 279. The field memory 228 executes reading of video signals for one frame. Thus, a frozen picture is displayed, and the release signal shown in FIG. 24e is transferred to the camera 276 through a delay device 281 and an inverter 282 to force the camera 276 to effect exposure of one frame.

In the above-described eighth embodiment, the timer 277 is activated by the switches SW2 and SW4, but may be activated by the output signal of an iris-open-signal generating means 285 such as that shown by a dot-dashed line in FIG. 17. The iris-open-signal generating means 285 is constituted by, for example, a photo-interrupter in which the light adjustment member (or iris) 214 shown in FIG. 17 inhibits light emitted by a light emitting device from entering a light receiving device when the iris 214 is retracted to a position at which the iris 214 does not shield the illuminating light (the light emitting device and the light receiving device are opposed to each other along the axis perpendicular to the sheet of FIG. 17). The timer 277 responds to the output signal of the iris-open-signal generating means and outputs the signal shown in FIG. 24d with a slight time lag. Incidentally, in this case, a delay device may be used in place of the timer 277. If a frozen picture is displayed, the duration of photography employing the freeze signal may be one field, one frame or a multiple thereof in synchronization with the display of the frozen picture.

In a case where a frozen picture is forcibly set by the timer output, the video level is compared with its initial level prior to reading of the frozen picture and its imaging time period (exposure time) is prolonged (for example, to a multiple of 1/600 seconds). Thereafter, a drive signal for a CCD readout operation may be applied, and signals which are then output may be read into the field memory.

Figure 25:
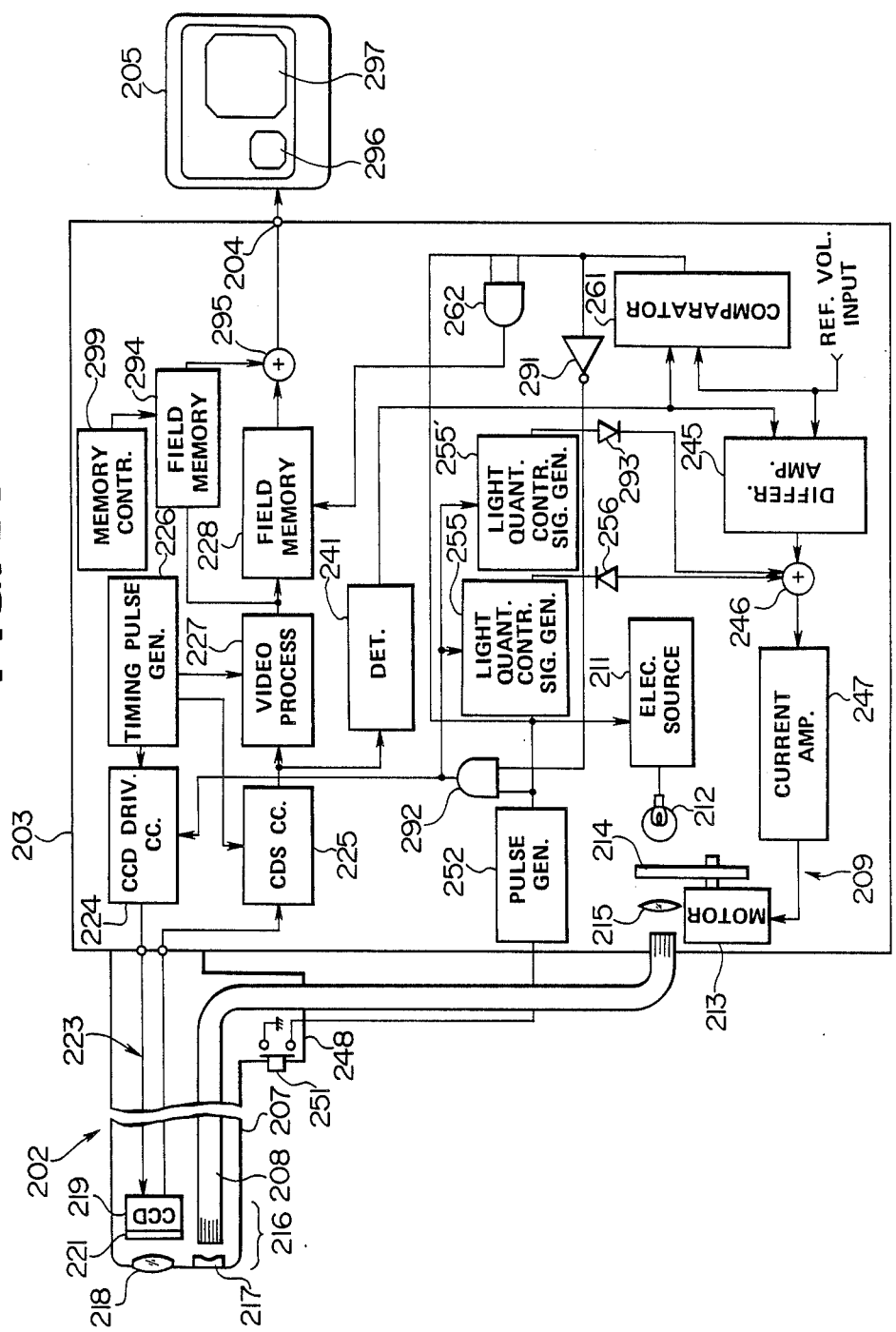
FIG. 25 is a block diagram of a video endoscope apparatus according to a ninth embodiment of the present invention.
Figure 26:
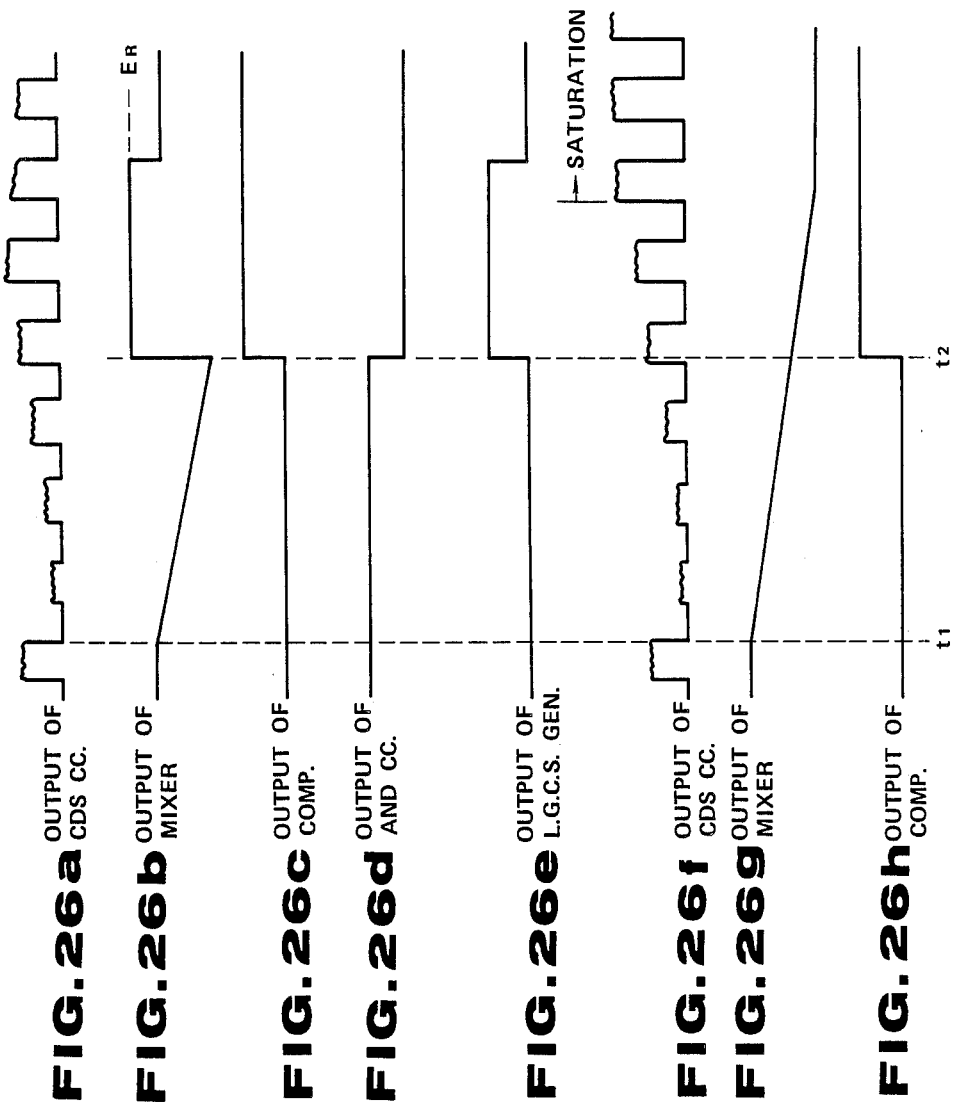
FIGS. 26a to 26h constitute a timing chart illustrating the operation of the ninth embodiment of the present invention.

FIG. 25 shows a ninth embodiment of the present invention, and FIG. 26 is a waveform diagram illustrating the operation of the ninth embodiment. This embodiment contemplates the solution of drawbacks occurring when a frozen picture and a motion picture are displayed at the same time.

In freezing using a device shutter, there are cases where two screens, a parent screen and a child screen, are output to an identical monitor and a frozen picture is output onto the parent screen with a motion picture being output onto the chile screen. If, in this case, the state of the device shutter is further continued after the completion of a freezing operation, a light adjustment device for the light source device is forcibly fully opened to compensate for a decrease in sensitivity in the case of long-distance photography. However, since the sensitivity decrease cannot be completely compensated for, the obtained motion picture becomes a dark one. For this reason, as shown in FIG. 25, the output of the comparator 261 is input as a reset pulse to an AND circuit 292 through an inverter 291. If the output of the comparator 261 goes to its high level, the output is set to its low level by the inverter 291 and input to the AND circuit 292, thereby preventing the output of the pulse generator 252 from being applied to the CCD driving circuit 224 and thereby resetting the state of CCD readout to its normal imaging mode.

When the normal imaging mode is reset, the charge storage time of the CCD 219 is reset to 1/60 seconds, but a proper exposure is not instantaneously reached due to the electrical or mechanical hysterisis of automatic exposure. However, substantial sensitivity abruptly increases and, as shown in FIG. 26f, the child picture is saturated. Incidentally, FIGS. 26g and 26h show the output of the mixer 246 and the output of the comparator 261, respectively.

In order to prevent the child picture from being saturated, a second light quantity control signal generator 255' is disposed which is driven by the output of the above-described AND circuit 292. At the falling edge of the output pulse, shown in FIG. 26d, of the AND circuit 292, the second light quantity control signal generator 255' outputs a light-quantity control signal with a pulse width of 50 msecs. and a voltage of about 3V, higher than a voltage $E_R$, as shown in FIG. 26e. Such a light-quantity control signal is input to the mixer 246 through a diode 293. In this manner, an operation acting to fully open the iris for the light source is controlled to suppress an abrupt rise in the output to the child screen. It is to be noted that, although the output of the light-quantity-control signal generator 255' is a signal of voltage higher than $E_R$ and pulse width of 50 msecs, the pulse width may be suitably selected so that no excessive control is provided over the iris for the light source.

In order to display a frozen picture and a motion picture, the output of the video processing circuit 227 is input to the field memory 228 for storing a parent picture and a field memory 294 for storing a child picture. The output signals read from the memories 228 and 294 are added in a mixer 295 and then applied to the color monitor 205. Similarly to the parent-picture field memory 228, the child-picture field memory 294 is constituted by, for example, an A/D converter, a RAM and a D/A converter. During reading, suitably selected readout addresses are applied to the child-picture field memory 294. Accordingly, the picture data thus read out constitutes a reduced picture. The reduction ratio is, for example, ¼ in terms of the area ratio of the child picture to the parent picture and, as shown in FIG. 25, a child-picture display section 296 and a parent-picture display section 297 are contiguously displayed on an identical screen. Incidentally, a memory controller 299 controls the readout of a reduced image and its timing of the field memory 294. Also, in a writing operation, suitably selected video signals may be read.

In accordance with the ninth embodiment, subsequently to time t1 at which the special imaging mode is selected, the respective outputs of the CDS circuit 224, the mixer 246, and the comparator 261 vary as shown in FIGS. 26a, 26b and 26c. At time t2 at which an initial video level is again reached, the output of the comparator 261 is switched from the low level to the high level, as shown in FIG. 26c. Simultaneously, the output of the AND circuit 292 is switched from the high state to the low state as shown in FIG. 26d, and this switched output causes the output of the light quantity control signal generator 255' to go from the low level to the high level. This high-level output is added to the mixer 246 to release the iris from its forcibly opened state, and the iris is forcibly stopped down. Accordingly, the output of the child picture, that is, the motion picture is prevented from abruptly increasing.

In accordance with the ninth embodiment, means is provided for setting the CCD driving circuit 224 to its normal imaging mode in response to a signal which is output from the comparator 261 and which is passed through the inverter 291, and for preventing the quantity of illuminating light from approaching its fully open level in response to the output of the light-quantity-control signal generator 255', whereby the child picture can be prevented from being saturated or continuously saturated.

Figure 27:
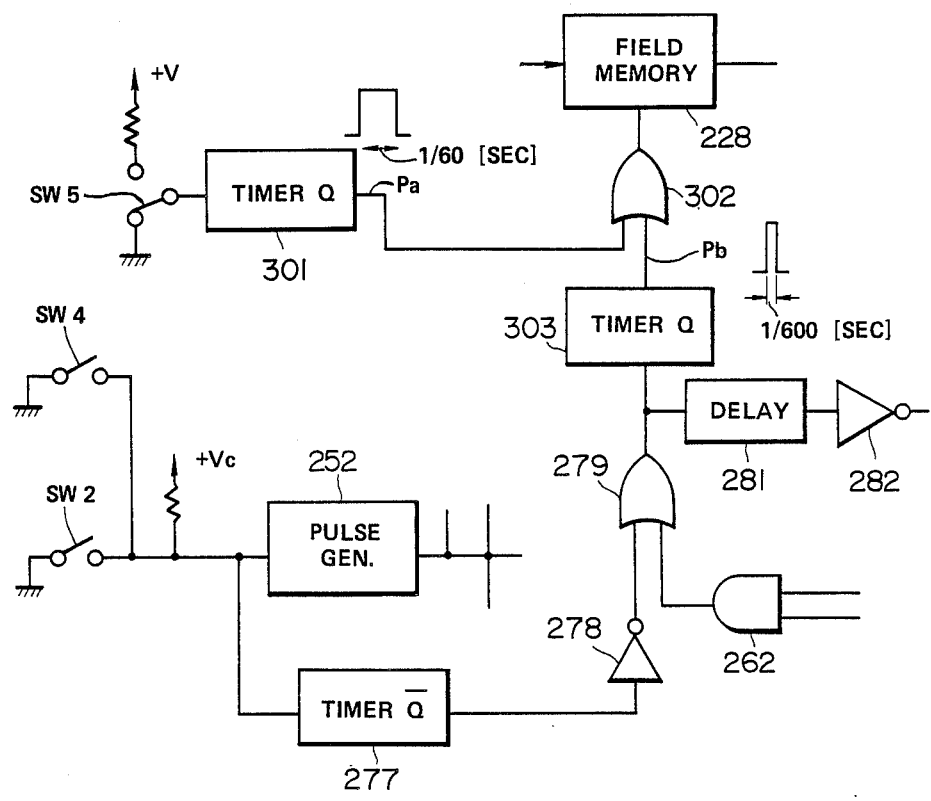
FIG. 27 is a block diagram showing the essential portion of a tenth embodiment of the present invention.

FIG. 27 shows the essential portion of a tenth embodiment of the present invention.

The tenth embodiment is a modified version of the eighth embodiment shown in FIG. 23 in that a frozen picture can be displayed in the normal mode as well. To this end, a freeze operation switch SW5 is added to the arrangement of the eighth embodiment. When the output of the switch SW 5 is switched from its high level to its low level, a timer (one-shot multivibrator) 301 is activated by the falling edge of the output to output a pulse Pa of, for example, 1/60 seconds. The pulse Pa is input to an OR circuit 302, and thus the field memory 228 is held in its write mode for 1/60 seconds alone. When the 1/60-second write mode is set, image data for one field is held in the field memory 228.

When the special mode is selected in this embodiment, the output of the AND circuit 262 is input to a timer 303 through an OR circuit 279, and the timer 303 outputs a write pulse Pb which is held in its high-level state for 1/600 seconds only. Thus, the field memory 228 reads out image data for one field.

Figure 28:
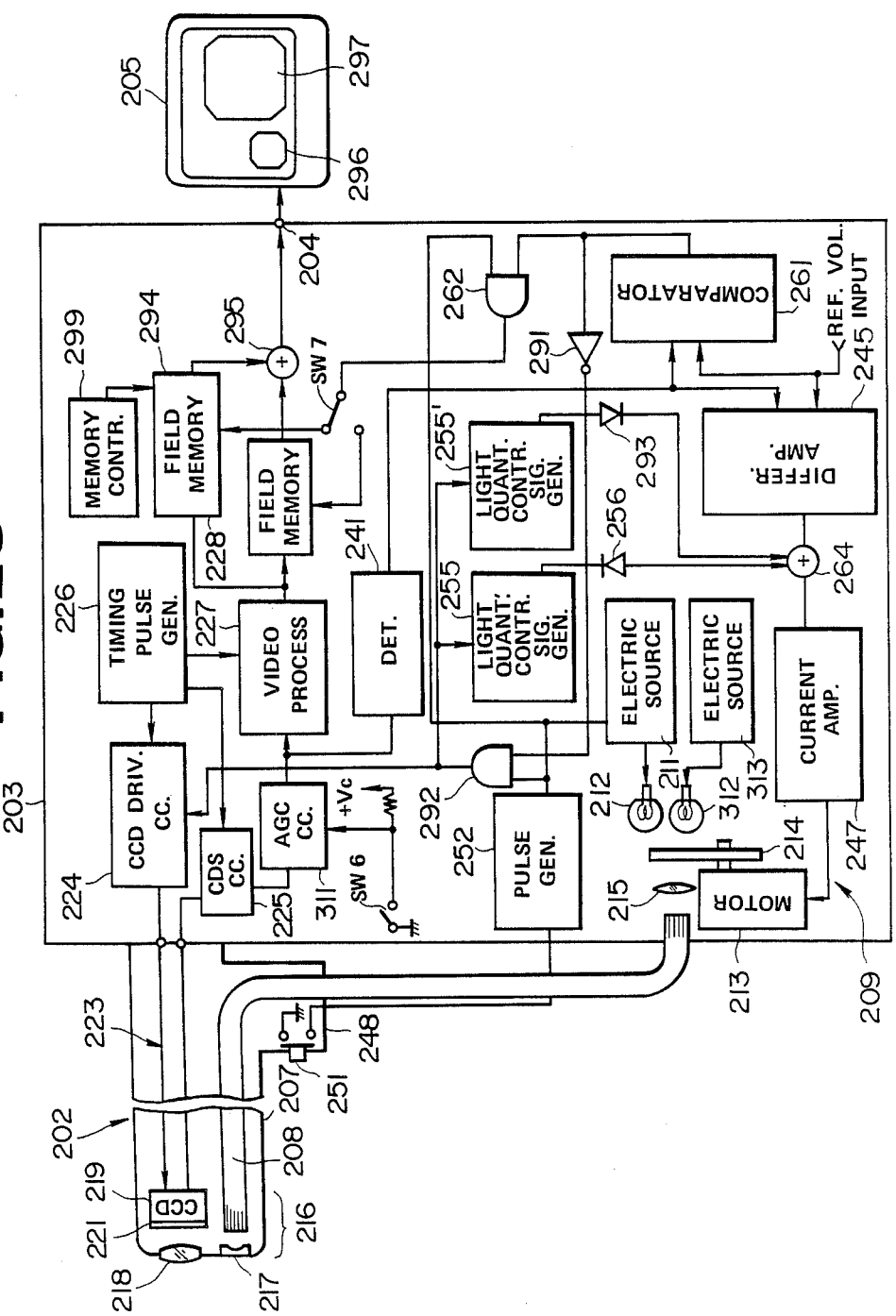
FIG. 28 is a block diagram showing an eleventh embodiment of the present invention.

FIG. 28 shows an eleventh embodiment of the present invention. This embodiment is a modified version of the ninth embodiment shown in FIG. 25 in that the output signal of the CDS circuit 22 is passed through an AGC circuit 311 and then supplied to the video processing circuit 227 and the detector 241. Since the AGC circuit 311 is added, even when the quantity of illuminating light supplied from the light source is insufficient, it is possible to set a proper exposure and hence to have a still picture produced by the device shutter. Incidentally, the AGC circuit 311 can be switched on or off by a switch SW6.

In this embodiment, the light source device 209 is provided with a plurality of lamps, that is, the lamp 212 as well as a lamp 312.

In this arrangement, the lamp 312 which is an ordinary continuously lighting lamp is continuously supplied with lighting electric power from an electric power source 313. The other lamp 212 is a lamp which produces flashes of light in association with a device shutter.

This embodiment is provided with a select switch SW7 for determining whether or not a still picture produced by the device shutter should be displayed. The aforesaid shutters SW6 and SW7 may be provided on the operating section 248.

FIG. 29 shows an electronic endoscope apparatus 321 according to a twelfth embodiment of the present invention.

This embodiment is a modified version of the seventh embodiment shown in FIG. 13 in that the output signals of the video processing circuit 227, that is, the video signals are applied from an external output terminal of the apparatus 321 to a video signal input terminal of a video disc 322 and the output of the AND circuit 262 is applied to a video recording control terminal as its recording trigger signal, whereby an image per field or frame can be recorded on the video disc 322.

The aforementioned video signals are input to a motion sensor 322, in which the discrepancy between these video signals and the video signals of the preceding field, that is, the motion of an image is detected. The motion sensor 322 supplies a signal according to the amount of motion to a shutter-velocity varying circuit 324 to control a timing pulse generator 226, thereby automatically controlling the shutter velocity to the value according to the amount of motion.

Figure 30:
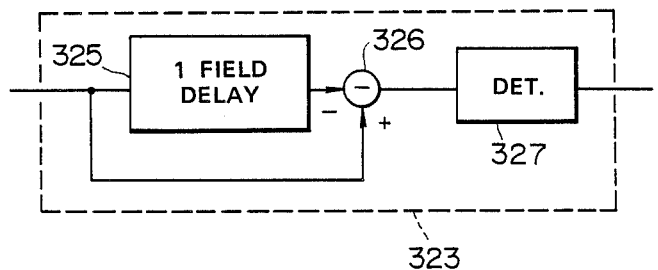
FIG. 30 is a block diagram showing the construction of a motion sensor for use in the twelfth embodiment.

The aforesaid motion sensor 323 has a construction such as that shown in, for example, FIG. 30.

More specifically, a video signal is applied to a one-field delay circuit 325, and the one-field delay circuit 325 outputs a video signal which has been delayed by one field. The one-field delayed signal is subtracted from a non-delayed video signal in a subtraction circuit 326, and the result is supplied to a detector circuit 327 and subjected to the detection thereof. Thus, a DC signal of magnitude substantially proportional to the amount of motion is generated.

The above-described shutter velocity varying circuit 324 controls the timing pulse generator 226 in accordance with the magnitude of the aforesaid DC signal, whereby the charge storage time of the CCD 219 is variably controlled. More specifically, as the amount of motion is large, the level of the dc signal is reduced. As this level is made smaller, the time interval required for a drive signal to be supplied from the timing pulse generator 226 to the CCD driving circuit 224 is shortened, whereby an image which is scarcely blurred can be recorded on the field memory 228 and the video disc 322.

The shutter velocity varying circuit 324 is provided with a switch SW8 for switching on or off the automatic shutter velocity control provided by the motion sensor 323. If the switch SW8 is switched off, a desired shutter velocity can be manually set by operating a shutter velocity select switch SW9.

The aforesaid video disc 322 may be a magnetic type of disc (a floppy disc or a hard disc), an optical type of disc, or any other medium that allows recording and reproducing of still pictures in units of fields or frames.

In each of the seventh to twelfth embodiments, an electronic scope is employed for the purpose of illustration only. However, the present invention is applicable to an electronic endoscope apparatus in which a television camera employing a solid state imaging device as imaging means is attached to the eyepiece portion of an optical type of scope.

It is to be noted that, in each of the above-described electronic and optical scopes, its inserting section may have, instead of a light guide, a lamp at its leading end.

Furthermore, if a portion of each of the above-described embodiments may be combined with the other, it is possible to constitute various modified forms.

What is claimed is:

1. A video endoscope apparatus comprising:
   (a) an electronic scope including:
      an elongated inserting section;
      light emitting means for emitting illuminating light through the leading end of said inserting section;
      an objective optical system disposed at said leading end of said inserting section for focusing an optical image; and
      imaging means including a solid state imaging device for effecting photoelectric conversion of said optical image focused by said objective optical system; and
   (b) charge-storage-time shortening means for shortening the storage time required for signals obtained by said photoelectric conversion of said solid state imaging device to be stored in the form of signal charges.

2. A video endoscope apparatus comprising:

(a) an electronic scope including:
   an elongated inserting section;
   light emitting means for emitting illuminating light through the leading end of said inserting section;
   an objective optical system disposed at said leading end of said inserting section for focusing an optical image of an object; and
   a solid state imaging device having a photoelectric conversion function and disposed in the focal plane of said objective optical system;

(b) a drive circuit for supplying said solid state imaging device with a drive signal for reading a signal therefrom;

(c) storage-time varying means for varying the storage time of said solid state imaging device in response to the drive signal supplied from said drive circuit;

(d) a video-signal processing circuit for generating a predetermined video signal by processing the signal read from said solid state imaging device by the application of said drive signal;

(e) memory means for storing therein signals output from said solid state imaging device;

(f) level comparing means for determining whether or not the level of said signals read from said solid state imaging device has coincided with a predetermined level;

(g) means for generating a write control signal to provide control so as to write said video signal into said memory means in response to a coincidence signal output from said level comparing means;

(h) illuminating-light-quantity varying means arranged to forcibly increase the quantity of illuminating light to be emitted from said light emitting means toward said object; and (i) trigger means for activating said storage-time varying means.

3. A video endoscope apparatus having an externally attached television camera, comprising:

(a) an optical endoscope including:
   an elongated inserting section;
   light emitting means for emitting illuminating light through the leading end of said inserting section;
   an objective optical system disposed at said leading end of said inserting section for focusing an optical image of an object;
   an image guide for transferring the optical image focused by said objective optical system; and
   an eyepiece section provided with an eyepiece window which allows observation of said optical image transferred through said image guide;

(b) a television camera detachably mounted to said eyepiece section and including a solid state imaging device having an focusing optical system and a photoelectric conversion device;

(c) a drive circuit for supplying said solid state imaging device with a drive signal for reading a signal therefrom;

(d) storage-time varying means for varying the storage time of said solid state imaging device in response to the drive signal supplied from said drive circuit;

(e) a video-signal processing circuit for generating a predetermined video signal by processing the signal read from said solid state imaging device by the application of said drive signal;

(f) memory means for storing therein signals output from said solid state imaging device;

(g) level comparing means for determining whether or not the level of said signals read from said solid state imaging device has coincided with a predetermined level;

(h) means for generating a write control signal to provide control so as to write said video signal into said memory means in response to a coincidence signal output from said level comparing means;

(i) illumination-quantity varying means arranged to forcibly increase the quantity of illuminating light to be emitted from said light emitting means toward an object; and (j) trigger means for activating said storage-time varying means.

4. A video endoscope apparatus comprising:

(a) an electronic scope including:
   an elongated inserting section;
   light emitting means for emitting illuminating light through the leading end of said inserting section;
   an objective optical system disposed at said leading end of said inserting section for focusing an optical image of an object; and
   a solid state imaging device having a photoelectric conversion function and disposed in the focal plane of said objective optical system;

(b) storage-time switching means for switching the duration of storage time to a short time period, said storage time being the period required for signals obtained by said photoelectric conversion of said solid state imaging device to be stored in the form of signal charges;

(c) illumination-light-quantity increasing means for increasing the quantity of illuminating light to be emitted from said light emitting means toward said object in response to a switching of said switching means;

(d) level detecting means for detecting the level of the photoelectrically converted output of said solid state imaging device after said solid state imaging device has effected a imaging operation using said illumination-light-quantity increasing means; and (e) storage means for storing video signals supplied from from said solid state imaging device when said level of said photoelectrically converted output detected by said level detecting means is within an allowable level.

5. A video endoscope apparatus comprising:

(a) an electronic scope including:
   an elongated inserting section;
   light emitting means for emitting illuminating light through the leading end of said inserting section;
   an objective optical system disposed at said leading end of said inserting section for focusing an optical image; and
   imaging means including a solid state imaging device for effecting photoelectric conversion of said optical image supplied from said objective optical system;

(b) charge-storage-time shortening means for shortening the storage time required for signals obtained by said photoelectric conversion of said solid state imaging device to be stored in the form of signal charges;

(c) picture storing means capable of storing the signals which have been photoelectrically converted in said solid state imaging device under said illuminating light emitted by said light emitting means; and (e) freeze switch means disposed at an operating section of said electronic scope for storing still pictures, each for one field or frame, in said picture storing means.

6. A video endoscope apparatus according to claim 1 or 4, wherein said electronic scope is an electronic scope in which said solid state imaging device is disposed in the focal plane of said objective optical system.

7. A video endoscope apparatus according to claim 1 or 4, wherein said electronic scope comprises an optical endoscope provided with an image guide for transmitting an optical image of said objective optical system and a television camera detachably mounted to an eyepiece section of said optical endoscope and including said solid state imaging device for effecting photoelectric conversion of said optical image transmitted through said image guide.

8. A video endoscope apparatus according to claim 4, further comprising an automatic gain control circuit for amplifying the output signal of said solid state imaging device, said automatic gain control circuit arranged to output its output signal to said level detecting means.

9. A video endoscope apparatus according to claim 2, 3 or 4, further comprising display means for displaying said video signal on its display screen.

10. A video endoscope apparatus according to claim 9, further comprising a still camera arranged to photograph an image of said object displayed on the display screen of said display means.

11. A video endoscope apparatus according to claim 1 or 4, further comprising recording means for recording said video signal.

12. A video endoscope apparatus according to claim 9, further comprising release-signal outputting means for outputting a release signal to release the shutter of said still camera.

13. A video endoscope apparatus according to claim 2 or 3, wherein said trigger means includes an activating switch and a pulse generator for outputting an activating pulse of duration no less than the period which starts at the time instant of the operation of said activating switch and lasts until said illuminating-light-quantity varying means has increased said quantity of illuminating light to a maximum level.

14. A video endoscope apparatus according to claim 2, 3 or 4, wherein said trigger means includes an iris provided with an aperture, a light shielding portion, and iris driving means for increasing the quantity of illuminating light passing through said aperture by shifting said iris.

15. A video endoscope apparatus according to claim 2, 3 or 4, wherein said illuminating-light-quantity varying means is arranged to increase the intensity of emission by increasing driving electric power to be supplied to said light emitting means.

16. A video endoscope apparatus according to claim 2, 3 or 4, wherein said illuminating-light-quantity varying means is arranged to increase the intensity of emission by causing both a continuously lighting lamp and a flash lamp to emit light.

17. A video endoscope apparatus according to claim 14, wherein said illuminating-light-quantity varying means further includes means for increasing the intensity of emission of a lamp for projecting light on said iris.

18. A video endoscope apparatus according to claim 2 or 3, wherein said means for generating a write control signal is arranged to forcibly output said write control signal subsequently to a time instant at which said illuminating-light-quantity varying means sets the quantity of illuminating light to its maximum level.

19. A video endoscope apparatus according to claim 2, 3 or 4, wherein said illuminating-light-quantity varying means is arranged to set the quantity of illuminating light to its maximum level in accordance with a time constant which is at least several times said storage period.

20. A video endoscope apparatus according to claim 18, wherein said means for forcibly outputting said write control signal is constituted by a timer.

21. A video endoscope apparatus according to claim 18, wherein said means for forcibly outputting said write control signal is constituted by a position sensor for detecting the fully opened state of said iris provided with said aperture and said light shielding portion.

22. A video endoscope apparatus according to claim 2 or 3, wherein said trigger means is disposed in said video signal processing circuit.

23. A video endoscope apparatus according to claim 2 or 3, further comprising a freeze switch operated to write video signal data for one field or one frame into said memory means when said illuminating-light-quantity varying means is not in operation.

24. A video endoscope apparatus according to claim 1, 2, 3, 4 or 5., wherein said solid state imaging device has a color separating filter device disposed on its light receiving surface.

25. A video endoscope apparatus according to claim 2, 3 or 4, wherein said illuminating-light-quantity varying means further includes a differential amplifier for providing a difference signal by comparing the level of said video signal with a reference level and automatic light adjusting means for automatically controlling the quantity of illuminating light emitted from said light emitting means by increasing or decreasing the intensity of the light of said lamp in accordance with the level of the output signal of said differential amplifier.

26. A video endoscope apparatus according to claim 2 or 3, wherein said video signal processing circuit includes a reduced-picture-signal producing circuit for displaying a reduced motion picture and mixing means for mixing video signals representing a picture reduced by said reduced-picture-signal producing circuit with frozen-picture signals read from said memory means.

27. A video endoscope apparatus according to claim 26, further comprises means for releasing an increase in the quantity of illuminating light which has been forcibly increased by said illuminating-light-quantity varying means 28. A video endoscope apparatus according to claim 2 or 3, wherein said memory means is a semiconductor memory for storing composite video signals for one field or frame.

29. A video endoscope apparatus according to claim 2 or 3, wherein said memory means is a video disc device for storing composite video signals.

30. A video endoscope apparatus according to claim 8, further comprising switch means for switching on and off said automatic gain control circuit.

31. A video endoscope apparatus according to claim 1, further comprising motion detecting means for examining the correlation between the output signal of said solid state imaging device and a delayed signal obtained by delaying said output signal by a predetermined time and means for variably controlling the storage time of said charge-storage-time shortening means in accordance with the output signal of said motion detecting means.

32. A video endoscope apparatus according to claim 2 or 3, further comprising motion detecting means for examining the correlation between the output signal of said solid state imaging device and a delayed signal obtained by delaying said output signal by a multiple of one field or frame and means for variably controlling said charge-storage-time in accordance with the output signal of said motion detecting means.

* * * * *